United States Patent [19]
Steinman et al.

[11] Patent Number: 5,667,967
[45] Date of Patent: Sep. 16, 1997

[54] T-CELL RECEPTOR VARIBLE TRANSCRIPTS AS DISEASE RELATED MARKERS

[75] Inventors: Lawrence Steinman; Jorge Oksenberg, both of Palo Alto, Calif.; Claude Bernard, North Baldwin, Australia

[73] Assignee: The Board of Trustees of the Leland Stanford Junior University, Stanford, Calif.

[21] Appl. No.: 66,325

[22] Filed: May 21, 1993

Related U.S. Application Data

[63] Continuation of Ser. No. 877,444, Apr. 30, 1992, abandoned, which is a continuation-in-part of Ser. No. 517,245, May 1, 1990, abandoned and PCT/US91/02991, May, 1, 1991, published as WO92/21367.

[51] Int. Cl.$^6$ .............................. C12P 19/34; C12Q 1/68
[52] U.S. Cl. ............................. 435/6; 435/91.2; 935/77; 935/78
[58] Field of Search .......................... 435/6, 91, 91.2; 935/77, 78

[56] References Cited

U.S. PATENT DOCUMENTS 4,886,743  12/1989  Hood et al. .............................. 435/7.1

FOREIGN PATENT DOCUMENTS

WO 91/17268  11/1991  WIPO .............................. C12Q 1/68
WO 92/21367  12/1992  WIPO .............................. A61K 37/02
WO 93/12814  7/1993  WIPO .............................. A61K 39/00

OTHER PUBLICATIONS

Esch et al., "Observations, Legends, and Conjectures Concerning Restricted T–Cell Receptor Usage and Autoimmune Disease," *Critical Reviews in Immunology*, 11(5):249–264, 1992.

Oksenberg et al., "Selection for T–cell receptor Vβ–Dβ–Jβ gene rearrangements with specificity for a myelin basic protein peptide in brain lesions of multiple sclerosis," *Nature* 362:68–70, 1993.

Urban et al., "Restricted Use of T Cell Receptor V Genes in Murine Autoimmune Encephalomyelitis Raises Possibilities for Antibody Therapy,"*Cell* 54:577–592, 1988.

Chothia et al., "The outline structure of the T–cell αβ receptor," *EMBO Journal* 7(12): 3745–3755, 1988.

Claverie et al., "Implications of a Fab–like structure for the T–cell receptor," *Immunology Today* 10(1): 10–14, 1989.

Davis and Bjorkman, "T–cell antigen receptor genes and T–cell recognition," *Nature* 334: 395–402, 1988.

Hedrick et al., "Selection of Amino Acid Sequences in the Beta Chain of the T Cell Antigen Receptor," *Science* 239: 1541–1544, 1988.

Nalefski et al., "Amino Acid Substitutions in the First Complementarity–determining Region of a Murine T–cell Receptor α Chain Affect Antigen–Major Histocompatibility Complex Recognition," *Journal of Biological Chemistry* 265(15): 8842–8846, 1990.

Barrett, *Textbook of Immunology*, The CV Mosby Co., St. Louis, 1988, pp. 373–374.

Yamamura et al., "T–Cell Receptor CDR3 Homology among T Lymphocytes Capable of Inducing Autoimmune Encephalomyelitis," *Neurology* 43(4) S2:A411–A412, 1993.

Brostoff and Howell, "T Cell Receptors, Immunoregulation, and Autoimmunity," *Clin. Immunol. and Immunop.* 62(1):1–7, 1992.

Gold et al., "Characterization of the Immune Response to a Secondary Encephalitogenic Epitope of Basic Protein in Lewis Rats," *J. Immunol.* 148(6):1712–1717, 1992.

Martin et al., "Diversity in Fine Specificity and T Cell Receptor Usage of the Human CD4+ Cytotoxic T Cell Response Specific for the Immunodominant Myelin Basic Protein Peptide 87–106," *J. Immunol.* 148(5):1359–1366, 1992.

Martin et al., "A Myelin Basic Protein Peptide Is Recognized by Cytotoxic T Cells in the Context of Four HLA–DR Types Associated with Multiple Sclerosis," *J. Exp. Med.* 173:19–24, 1991.

Oksenberg et al., "T–cell receptor Vα and Cα alleles associated with multiple sclerosis and myasthenia gravis," *Proc. Natl. Acad. Sci. USA* 86:988–992, 1989.

Acha–Orbea et al., "Limited Heterogeneity of T Cell Receptors from Lymphocytes Mediating Autoimmune Encephalomyelitis Allows Specific Immune Intervention," *Cell* 54:263–273, 1988.

Stamenkovic et al., "Clonal dominance among T–lymphocyte infiltrates in arthritis," *Pro. Natl. Acad. Sci. USA* 85:1179–1183, 1988.

Toyonaga and Mak, "Genes of the T–Cell Antigen Receptor in Normal and Malignant T Cells," *Ann. Rev. Immunol.* 5:585–620, 1987.

Minden et al., "Somatic rearrangment of T–cell antigen receptor gene in human T–cell malignancies," *Pro. Natl. Acad. Sci. USA* 82:1224–1227, 1985.

Burns et al., "Isolation of Myelin Basic Protein–Reactive T–Cell Lines from Normal Human Blood," *Cell. Immunol.* 81:435–440, 1983.

Oksenberg et al., PNAS(USA)86: 988–992 (Feb. 1989).

Acha–Orbea et al., Cell 54:263–273 (Jun. 15, 1988).

Davis et al., Nature 334:395–402 (Aug. 4, 1988).

*Primary Examiner*—Stephanie W. Zitomer
*Attorney, Agent, or Firm*—Seed and Berry LLP

[57] ABSTRACT

Methods are provided for determining relations between autoimmune degenerative diseases and specific variable regions of T-cell receptors as associated with the host HLA or T-cells associated with umbatting neoprofilerative diseases. By identifying the particular T-cell receptors which cause or are the disease in mammals, various prophylactic and therapeutic techniques may be employed for inhibiting the attack of the T-cell receptors on the native protein or tissue enhance the defense. In addition, individuals may be diagnosed as to their propensity for a particular autoimmune disease or the occurrence of such a disease.

6 Claims, No Drawings

SEQUENCE LISTING ( 1 ) GENERAL INFORMATION:

( i i i ) NUMBER OF SEQUENCES: 157

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGGTACCGAG ATGACGAACC CACCTTTGGG ACAGGCACTC AGCTAAAAGT GCAACTC    57

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu Cys Ala Ser Ser
1              5

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AGCCTACGCA GCTTGCGCAG CCTGCGGTTG CGC    33

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTGCCCTGAG AGATGCCAGA G    21

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GTGTTCCCAG AGGGAGCCAT TGCC                                                24
```

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GGTGAACAGT CAACAGGGAG A                                                   21
```

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
ACAAGCATTA CTGTACTCCT A                                                   21
```

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
GGCCCTGAAC ATTCAGGA                                                       18
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GTCACTTTCT AGCCTGCTGA                                                     20
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
AGGAGCCATT GTCCAGATAA A                                                   21
```

( 2 ) INFORMATION FOR SEQ ID NO:11:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:11:

GGAGAGAATG TGGAGCAGCA TC 22

( 2 ) INFORMATION FOR SEQ ID NO:12:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:12:

ATCTCAGTGC TTGTGATAAT A 21

( 2 ) INFORMATION FOR SEQ ID NO:13:

( i ) SEQUENCE CHARACTERISTICS:
 ( A ) LENGTH: 24 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:13:

ACCCAGCTGG TGGAGCAGAG CCCT 24

( 2 ) INFORMATION FOR SEQ ID NO:14:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:14:

AGAAAGCAAG GACCAAGTGT T 21

( 2 ) INFORMATION FOR SEQ ID NO:15:

( i ) SEQUENCE CHARACTERISTICS:
 ( A ) LENGTH: 24 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:15:

CAGAAGGTAA CTCAAGCGCA GACT 24

( 2 ) INFORMATION FOR SEQ ID NO:16:

( i ) SEQUENCE CHARACTERISTICS:
 ( A ) LENGTH: 19 base pairs
 ( B ) TYPE: nucleic acid
 ( C ) STRANDEDNESS: single (D) TOPOLOGY: linear (ii) MOLECULE TYPE: cDNA (xi) SEQUENCE DESCRIPTION: SEQ ID NO:16:

GCTTATGAGA ACACTGCGT 19

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCAGCTTCCC TTCCAGCAAT 20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGAACCTGAC TGCCCAGGAA 20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CATCTCCATG GACTCATATG A 21

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GACTATACTA ACAGCATGT 19

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TGTCAGGCAA TGACAAGG                                                                                                      18

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

AATAGGTCGA CACACTTGTC ACTGGA                                                                                             26

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

ACGAAGACGG ACCACCGCCC TG                                                                                                 22

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

CACGTTGTGG GTGACGCCGT C                                                                                                  21

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CAGAAGGTAA CTGCAGCGCA GACT                                                                                               24

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

TTGGGGATCC AGAGCACAGA AGTATACTGC                                                                                         30

( 2 ) INFORMATION FOR SEQ ID NO:27:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:27:

CAGAACCCTG ACCCTGCCGT GTAC                                                                  24

( 2 ) INFORMATION FOR SEQ ID NO:28:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:28:

GTGTCCACAG TTTAGGTTCG TATCTGT                                                               27

( 2 ) INFORMATION FOR SEQ ID NO:29:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:29:

CTGGAGCTCC TGTAGAAGGA G                                                                     21

( 2 ) INFORMATION FOR SEQ ID NO:30:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:30:

CAGAACCCTG ACCCTGCCGT GTAC                                                                  24

( 2 ) INFORMATION FOR SEQ ID NO:31:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:31:

GCACAACAGT TCCCTGACTT GCAC                                                                  24

( 2 ) INFORMATION FOR SEQ ID NO:32:

( i ) SEQUENCE CHARACTERISTICS:
    ( A ) LENGTH: 24 base pairs
    ( B ) TYPE: nucleic acid
    ( C ) STRANDEDNESS: single ( D ) TOPOLOGY: linear ( i i ) MOLECULE TYPE: cDNA ( x i ) SEQUENCE DESCRIPTION: SEQ ID NO:32:

TCATCAACCA TGCAAGCCTG ACCT                                           24

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

GTCTCTAGAG AGAAGAAGGA GCGC                                           24

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

ACGATCCAGT GTCAAGTCGT                                                20

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

ATACTTCAGT GAGACACAGA GA                                             22

( 2 ) INFORMATION FOR SEQ ID NO:36:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

TTCCCTAACT ATAGCTCTGG CTG                                            23

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

AGGCCTGAGG GATCCGTCTC 20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CCTGAATGCC CCAACAGCTC TC 22

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

ACTTTAACAA CAACGTTCCG A 21

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

CTAAATCTCC AGACAAAGCT CAC 23

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

TCCAAAAACT CATCCTGTAC CT 22

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

TGTTCTCAAA CCATGGGCCA TGAC 24

(2) INFORMATION FOR SEQ ID NO:43:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:43:

GATACTGACA AAGGAGAAGT CTCAGAT 27

( 2 ) INFORMATION FOR SEQ ID NO:44:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:44:

GGTGAGGGTA CAACTGCC 18

( 2 ) INFORMATION FOR SEQ ID NO:45:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:45:

ACCCAAGATA CCTCATCACA G 21

( 2 ) INFORMATION FOR SEQ ID NO:46:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:46:

AGTGTCTCTC GACAGGCACA G 21

( 2 ) INFORMATION FOR SEQ ID NO:47:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:47:

CATGATAATC TTTATCGACG TGTT 24

( 2 ) INFORMATION FOR SEQ ID NO:48:

( i ) SEQUENCE CHARACTERISTICS:
  ( A ) LENGTH: 25 base pairs
  ( B ) TYPE: nucleic acid
  ( C ) STRANDEDNESS: single (D) TOPOLOGY: linear (ii) MOLECULE TYPE: cDNA (xi) SEQUENCE DESCRIPTION: SEQ ID NO:48:

AGCCCAATGA AAGGAACACA GTCAT    25

(2) INFORMATION FOR SEQ ID NO:49:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:49:

AGCCCAATGA AAGGACACAG TCAT    24

(2) INFORMATION FOR SEQ ID NO:50:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:50:

ACCCCGAAA AAGGACATAC T    21

(2) INFORMATION FOR SEQ ID NO:51:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:51:

CTCTGAGGTG CCCCAGAA    18

(2) INFORMATION FOR SEQ ID NO:52:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:52:

TTCTGATGGC TCAAACAG    18

(2) INFORMATION FOR SEQ ID NO:53:

(i) SEQUENCE CHARACTERISTICS:
  (A) LENGTH: 28 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:53:

```
Leu Cys Ala Ser Ser Leu Pro Gly Thr Pro Tyr Gly Tyr Phe Gly Ser
1               5                   10                  15

Gly Thr Arg Leu Thr Val Val Glu Asp Leu Lys Asn
            20                  25
```

( 2 ) INFORMATION FOR SEQ ID NO:54:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

```
Leu Cys Ala Ser Ser Leu Pro Gly Thr Pro Tyr Gly Tyr Thr Phe Gly
1               5                   10                  15

Ser Gly Thr Arg Leu Thr Val Val Glu Asp Leu Asn Lys
            20                  25
```

( 2 ) INFORMATION FOR SEQ ID NO:55:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
Leu Cys Ala Ser Ser Leu Arg Leu Ala Asn Ser Pro Leu His Phe Gly
1               5                   10                  15

Asn Gly Thr Arg Leu Thr Val Thr Glu Asp Leu Asn Lys
            20                  25
```

( 2 ) INFORMATION FOR SEQ ID NO:56:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Leu Cys Ala Ser Ser Leu Asp Arg Leu Tyr Asn Ser Pro Leu His Phe
1               5                   10                  15

Gly Asn Gly Thr Arg Leu Thr Val Thr Glu Asp Leu Asn Lys
            20                  25                  30
```

( 2 ) INFORMATION FOR SEQ ID NO:57:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Leu Cys Ala Ser Gln Leu Arg Leu Ala Asn Ser Pro Leu His Phe Gly
1               5                   10                  15
```

```
        Asn Gly Thr Arg Leu Thr Val Thr Glu Asp Leu Asn Lys
                 20                  25
```

( 2 ) INFORMATION FOR SEQ ID NO:58:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
        Leu Cys Ala Ser Ser Gln Leu Arg Leu Ala Asn Ser Pro Leu His Phe
        1               5                   10                      15

Gly Asn Gly Thr Arg Leu Thr Val Thr Glu Asp Leu Asn Lys
                        20                  25                  30
```

( 2 ) INFORMATION FOR SEQ ID NO:59:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
        Leu Cys Ala Ser Ser Phe Leu Gly Tyr Asn Ser Pro Leu His Phe Gly
        1               5                   10                      15

Asn Gly Thr Arg Leu Thr Val Thr Glu Asp Leu Asn Lys
                        20                  25
```

( 2 ) INFORMATION FOR SEQ ID NO:60:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
        Leu Cys Ala Ser Ser Gln Pro Thr Val Tyr Asn Asn Glu Gln Phe Phe
        1               5                   10                      15

Gly Gln Arg Thr Arg Leu Leu Val Leu Glu Asp Leu Lys Asn
                        20                  25                  30
```

( 2 ) INFORMATION FOR SEQ ID NO:61:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

```
        Leu Cys Ala Ser Ser Ser Asp Gly Arg Met Ser Thr Gln Tyr Phe Gly
        1               5                   10                      15

Pro Gly Thr Arg Leu Leu Val Leu Glu Asp Leu Lys Asn
                        20                  25
```

( 2 ) INFORMATION FOR SEQ ID NO:62:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

```
Leu Cys Ala Ser Ser Leu Val Ala Gly Ser Ile Tyr Glu Gln Tyr Phe
1               5                   10                  15
Gly Pro Gly Thr Arg Leu Thr Val Thr Glu Asp Leu Lys Asn
            20                  25                  30
```

( 2 ) INFORMATION FOR SEQ ID NO:63:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

```
Leu Cys Ala Ser Ser Ser Glu Arg Glu Gly Arg Ala Gln Tyr Phe Gly
1               5                   10                  15
Gln Gly Thr Arg Leu Thr Val Leu Glu Asp Leu Lys Asn
            20                  25
```

( 2 ) INFORMATION FOR SEQ ID NO:64:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

```
Leu Cys Ala Ser Ser Gly Gly Glu Gly Arg Ala Gln Tyr Phe Gly Gln
1               5                   10                  15
Gly Thr Arg Leu Thr Val Leu Glu Asp Leu Lys Asn
            20                  25
```

( 2 ) INFORMATION FOR SEQ ID NO:65:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

```
Leu Cys Ala Ser Ser Leu Asp Gly Val Pro Tyr Gly Tyr Thr Phe Gly
1               5                   10                  15
Ser Gly Thr Gly Leu Thr Val Val Glu Asp Leu Asn Lys
            20                  25
```

( 2 ) INFORMATION FOR SEQ ID NO:66:

( i ) SEQUENCE CHARACTERISTICS:
        ( A ) LENGTH: 29 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:66:

Leu Cys Ala Ser Ser Leu Asp Gly Val Pro Tyr Gly Tyr Thr Phe Gly
1               5                   10                  15
Ser Gly Thr Arg Leu Thr Val Val Glu Asp Leu Asn Lys
            20                  25

(2) INFORMATION FOR SEQ ID NO:67:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:67:

Leu Cys Ala Ser Ser Leu Asp Gly Val Asn Tyr Gly Tyr Thr Phe Gly
1               5                   10                  15
Ser Gly Thr Arg Leu Thr Val Val Glu Asp Leu Asn Lys
            20                  25

(2) INFORMATION FOR SEQ ID NO:68:

(i) SEQUENCE CHARACTERISTICS:
    (A) LENGTH: 30 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:68:

Leu Cys Ala Ser Ser Leu Val Gly Arg Gly Pro Tyr Gly Tyr Thr Phe
1               5                   10                  15
Gly Ser Gly Thr Arg Leu Thr Val Val Glu Asp Leu Asn Lys
            20                  25                  30

(2) INFORMATION FOR SEQ ID NO:69:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:69:

Leu Cys Ala Ser Ser Leu Gly Gly Val Pro Tyr Gly Tyr Thr Phe Gly
1               5                   10                  15
Ser Gly Thr Gly Leu Thr Val Val Glu Asp Leu Asn Lys
            20                  25

(2) INFORMATION FOR SEQ ID NO:70:

(i) SEQUENCE CHARACTERISTICS:
    (A) LENGTH: 29 amino acids
    (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO:70:

Leu Cys Ala Ser Ser Leu Arg Gly Thr Pro Tyr Gly Tyr Thr Phe Gly
1               5                   10                  15

Ser Gly Thr Arg Leu Thr Val Val Glu Asp Leu Asn Lys
            20                  25

( 2 ) INFORMATION FOR SEQ ID NO:71:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:71:

Leu Cys Ala Ser Ser Gln Pro Ala Val Tyr Asn Glu Gln Phe Phe Gly
1               5                   10                  15

Pro Gly Thr Arg Leu Thr Val Leu Glu Asp Leu Lys Asn
            20                  25

( 2 ) INFORMATION FOR SEQ ID NO:72:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:72:

Leu Cys Ala Ser Ser Leu Glu Leu Ala Gly Tyr Asn Glu Gln Phe Phe
1               5                   10                  15

Gly Pro Gly Thr Arg Leu Thr Val Leu Glu Asp Leu Lys Asn
            20                  25                  30

( 2 ) INFORMATION FOR SEQ ID NO:73:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:73:

Leu Cys Ala Ser Ser Leu Gly Gly Ser Glu Glu Asp Thr Gln Tyr Phe
1               5                   10                  15

Gly Pro Gly Thr Arg Leu Thr Val Leu Glu Asp Leu Lys Asn
            20                  25                  30

( 2 ) INFORMATION FOR SEQ ID NO:74:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:74:

```
Leu Cys Ala Ser Ser Leu Gly Gly Ser Glu Glu Thr Gln Tyr Phe Gly
1               5                   10                  15

Pro Gly Thr Arg Leu Leu Val Leu Glu Asp Leu Lys Asn
            20                  25
```

(2) INFORMATION FOR SEQ ID NO:75:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:75:

```
Leu Cys Ala Ser Ser Leu Gly Gly Ser Val Glu Thr Gln Tyr Phe Gly
1               5                   10                  15

Pro Gly Thr Arg Leu Leu Val Leu Glu Asp Leu Lys Asn
            20                  25
```

(2) INFORMATION FOR SEQ ID NO:76:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:76:

```
Leu Cys Ala Ser Ser Leu Ala Ser Gly Thr Leu Gln Glu Thr Gln Tyr
1               5                   10                  15

Phe Gly Pro Gly Thr Arg Leu Leu Val Leu Glu Asp Leu Lys Asn
                20                  25                  30
```

(2) INFORMATION FOR SEQ ID NO:77:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:77:

```
Leu Cys Ala Ser Ser Leu Ala Ser Gly Thr Leu Gln Glu Thr Gln Tyr
1               5                   10                  15

Phe Gly Pro Gly Thr Arg Leu Leu Val Leu Glu Asp Leu Lys Asn
                20                  25                  30
```

(2) INFORMATION FOR SEQ ID NO:78:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:78:

```
Leu Cys Ala Ser Ser Leu Ala Ser Gly Thr Leu Gln Glu Thr Gln Tyr
1               5                   10                  15

Phe Gly Pro Gly Thr Arg Leu Leu Val Leu Glu Asp Leu Lys Asn
```

|  | 20 | 25 | 30 |
|---|---|---|---|

( 2 ) INFORMATION FOR SEQ ID NO:79:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Leu  Cys  Ala  Ser  Ser  Pro  Thr  Gly  Ala  Asn  Val  Leu  Thr  Phe  Gly  Ala
1                  5                        10                       15

Gly  Ser  Arg  Leu  Thr  Val  Leu  Glu  Asp  Leu  Lys  Asn
               20                       25
```

( 2 ) INFORMATION FOR SEQ ID NO:80:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Leu  Cys  Ala  Ser  Ser  Pro  Thr  Gly  Ala  Asn  Val  Leu  Thr  Phe  Gly  Ala
1                  5                        10                       15

Gly  Ser  Arg  Leu  Thr  Val  Leu  Glu  Asp  Leu  Lys  Asn
               20                       25
```

( 2 ) INFORMATION FOR SEQ ID NO:81:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

```
Leu  Cys  Ala  Ser  Ser  Gln  Gly  Ser  Thr  Phe  Gly  Ala  Gly  Ser  Arg  Leu
1                  5                        10                       15

Thr  Val  Leu  Glu  Asp  Leu  Lys  Asn
               20
```

( 2 ) INFORMATION FOR SEQ ID NO:82:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:82:

```
Leu  Cys  Ala  Ser  Ser  Ser  Gly  Ala  Asn  Val  Leu  Thr  Phe  Gly  Ala  Gly
1                  5                        10                       15

Ser  Arg  Leu  Thr  Val  Leu  Glu  Asp  Leu  Lys  Asn
               20                       25
```

( 2 ) INFORMATION FOR SEQ ID NO:83:

( i ) SEQUENCE CHARACTERISTICS:
   ( A ) LENGTH: 27 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:83:

Leu Cys Ala Ser Ser Leu Gly Ala Asn Val Leu Thr Phe Gly Ala Gly
1               5                   10                  15

Ser Arg Leu Thr Val Leu Glu Asp Leu Lys Asn
            20                  25

( 2 ) INFORMATION FOR SEQ ID NO:84:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:84:

Leu Cys Ala Ser Ser Leu Arg Gly Ala Asn Val Leu Thr Phe Gly Ala
1               5                   10                  15

Gly Ser Arg Leu Thr Val Leu Glu Asp Leu Lys Asn
                20                  25

( 2 ) INFORMATION FOR SEQ ID NO:85:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:85:

Leu Cys Ala Ser Ser Leu Val Ala Gly Ser Ile Tyr Glu Gln Tyr Phe
1               5                   10                  15

Gly Pro Gly Thr Arg Leu Thr Val Thr Glu Asp Leu Lys Asn
                20                  25                  30

( 2 ) INFORMATION FOR SEQ ID NO:86:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:86:

Leu Cys Ala Ser Ser Leu Val Ala Gly Ser Ile Tyr Glu Gln Tyr Phe
1               5                   10                  15

Gly Pro Gly Thr Arg Leu Thr Val Thr Glu Asp Leu Lys Asn
                20                  25                  30

( 2 ) INFORMATION FOR SEQ ID NO:87:

( i ) SEQUENCE CHARACTERISTICS:
      ( A ) LENGTH: 30 amino acids
      ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:87:

Leu Cys Ala Ser Ser Leu Val Ala Gly Ser Ile Tyr Glu Gln Tyr Phe
1               5                   10                  15

Gly Pro Gly Thr Arg Leu Thr Val Thr Glu Asp Leu Lys Asn
            20              25                  30

(2) INFORMATION FOR SEQ ID NO:88:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:88:

Leu Cys Ala Ser Thr Leu Arg Leu Gly Asn Ser Pro Leu His Phe Gly
1               5                   10                  15

Asn Gly Thr Arg Leu Thr Val Thr Glu Asp Leu Asn Lys
            20              25

(2) INFORMATION FOR SEQ ID NO:89:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:89:

Leu Cys Ala Ser Ser Asp Ser Ser Glu Thr Gln Tyr Phe Gly Pro Gly
1               5                   10                  15

Thr Arg Leu Leu Val Leu Glu Asp Leu Lys Asn
            20              25

(2) INFORMATION FOR SEQ ID NO:90:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:90:

Leu Cys Ala Ser Ser Leu Arg Gly Ala Asn Val Leu Thr Phe Gly Ala
1               5                   10                  15

Gly Ser Arg Leu Thr Val Leu Glu Asp Leu Lys Asn
            20              25

(2) INFORMATION FOR SEQ ID NO:91:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide ( x i ) SEQUENCE DESCRIPTION: SEQ ID NO:91:

Leu Cys Ala Ser Ser Leu Arg Gly Ala Asn Val Leu Thr Phe Gly Ala
1               5                   10                  15

Gly Ser Arg Leu Thr Val Leu Glu Asp Leu Lys Asn
            20                  25

( 2 ) INFORMATION FOR SEQ ID NO:92:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:92:

Leu Cys Ala Ser Ser Pro Thr Gly Ala Asn Val Leu Thr Phe Gly Ala
1               5                   10                  15

Gly Ser Arg Leu Thr Val Leu Glu Asp Leu Lys Asn
            20                  25

( 2 ) INFORMATION FOR SEQ ID NO:93:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:93:

Leu Cys Ala Ser Ser Leu Val Ala Gly Ile Tyr Glu Gln Tyr Phe Gly
1               5                   10                  15

Pro Gly Thr Arg Leu Thr Val Thr Glu Asp Leu Lys Asn
            20                  25

( 2 ) INFORMATION FOR SEQ ID NO:94:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:94:

Leu Cys Ala Ser Ser Leu Val Ala Gly Ser Ile Tyr Glu Gln Tyr Phe
1               5                   10                  15

Gly Pro Ser Thr Arg Leu Thr Val Thr Glu Asp Leu Lys Asn
            20                  25                  30

( 2 ) INFORMATION FOR SEQ ID NO:95:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:95:

Leu Cys Ala Ser Ser Leu Val Ala Gly Ser Ile Tyr Glu Gln Tyr Phe

```
             1               5                    10                       15

Gly Pro Ser Thr Arg Leu Thr Val Thr Glu Asp Leu Lys Asn
                         20                  25                  30
```

(2) INFORMATION FOR SEQ ID NO:96:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

```
         Leu Cys Ala Ser Ser Leu Gly Ser Pro Gly Tyr Arg Thr Asn Glu Lys
         1               5                   10                      15

Leu Phe Phe Gly Ser Gly Thr Gln Leu Ser Val Leu Glu Asp Leu Asn
                         20                  25                  30

Lys
```

(2) INFORMATION FOR SEQ ID NO:97:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

```
         Leu Cys Ala Ser Ser Phe Thr Gly Ala Tyr Tyr Asn Glu Gln Phe Phe
         1               5                   10                      15

Gly Pro Gly Thr Arg Leu Thr Val Leu Glu Asp Leu Lys Asn
                         20                  25                  30
```

(2) INFORMATION FOR SEQ ID NO:98:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
         Leu Cys Ala Ser Ser Arg Arg Thr Ser Gly Phe Val His Asp Thr Gln
         1               5                   10                      15

Tyr Phe Gly Pro Gly Thr Arg Leu Thr Val Leu Glu Asp Leu Lys Asn
                         20                  25                  30
```

(2) INFORMATION FOR SEQ ID NO:99:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
         Leu Cys Ala Ser Ala Arg Arg Thr Ser Gly Phe Val Thr Asp Thr Gln
         1               5                   10                      15
```

```
       Tyr Phe Gly Pro Gly Thr Arg Leu Thr Val Leu Glu Asp Leu Lys Asn
                20                  25                  30
```

( 2 ) INFORMATION FOR SEQ ID NO:100:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

```
       Leu Cys Ala Ser Thr Ala Arg Arg Thr Ser Gly Phe Val Thr Asp Thr
       1               5                   10                  15
       Gln Tyr Phe Gly Pro Gly Thr Arg Leu Thr Val Leu Glu Asp Leu Lys
                        20                  25                  30
       Asn
```

( 2 ) INFORMATION FOR SEQ ID NO:101:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:101:

```
       Leu Cys Ala Thr Ala Arg Arg Thr Ser Gly Phe Val Thr Asp Thr Gln
       1               5                   10                  15
       Tyr Phe Gly Pro Gly Thr Arg Leu Thr Val Leu Glu Asp Leu Lys Asn
                        20                  25                  30
```

( 2 ) INFORMATION FOR SEQ ID NO:102:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:102:

```
       Leu Cys Ala Thr Ala Arg Arg Thr Ser Gly Phe Val Thr Asp Thr Gln
       1               5                   10                  15
       Tyr Phe Gly Pro Gly Thr Arg Leu Thr Val Leu Glu Asp Leu Lys Asn
                        20                  25                  30
```

( 2 ) INFORMATION FOR SEQ ID NO:103:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:103:

```
       Leu Cys Ala Thr Ala Arg Arg Thr Ser Gly Phe Val Thr Asp Thr Gln
       1               5                   10                  15
       Tyr Phe Gly Pro Gly Thr Arg Leu Thr Val Leu Glu Asp Leu Lys Asn
                        20                  25                  30
```

( 2 ) INFORMATION FOR SEQ ID NO:104:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:104:

```
Leu Cys Ala Thr Ala Arg Arg Thr Ser Gly Phe Val Thr Asp Thr Gln
1               5                   10                  15

Tyr Phe Gly Pro Gly Thr Arg Leu Thr Val Leu Glu Asp Leu Lys Asn
                20                  25                  30
```

( 2 ) INFORMATION FOR SEQ ID NO:105:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

```
Leu Cys Ala Ser Arg Gln Gly Ala Arg Thr Gly Ala Asn Val Leu Thr
1               5                   10                  15

Phe Gly Ala Gly Ser Arg Leu Thr Val Leu Glu Asp Leu Lys Asn
                20                  25                  30
```

( 2 ) INFORMATION FOR SEQ ID NO:106:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:106:

```
Leu Cys Ala Ser Ser Val Ala Leu Gln Asp Arg Tyr Gly Tyr Thr Phe
1               5                   10                  15

Gly Ser Gly Thr Gly Leu Thr Val Val Glu Asp Leu Asn Lys
                20                  25              30
```

( 2 ) INFORMATION FOR SEQ ID NO:107:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:107:

```
Leu Cys Ala Ser Ser Thr Val Arg Gly Ser Gln Pro Gln His Phe Gly
1               5                   10                  15

Asp Gly Thr Arg Leu Ser Ile Leu Glu Asp Leu Asn Lys
                20                  25
```

( 2 ) INFORMATION FOR SEQ ID NO:108:

( i ) SEQUENCE CHARACTERISTICS:
: ( A ) LENGTH: 28 amino acids
: ( B ) TYPE: amino acid
: ( C ) STRANDEDNESS: single
: ( D ) TOPOLOGY: linear ( i i ) MOLECULE TYPE: peptide ( x i ) SEQUENCE DESCRIPTION: SEQ ID NO:108:

```
Leu Cys Ala Ser Ser Pro Gly Met Lys Asn Ile Gln Tyr Phe Gly Ala
1               5                   10                  15

Gly Thr Arg Leu Ser Val Leu Glu Asp Leu Lys Asn
            20                  25
```

( 2 ) INFORMATION FOR SEQ ID NO:109:

: ( i ) SEQUENCE CHARACTERISTICS:
:: ( A ) LENGTH: 30 amino acids
:: ( B ) TYPE: amino acid
:: ( C ) STRANDEDNESS: single
:: ( D ) TOPOLOGY: linear : ( i i ) MOLECULE TYPE: peptide : ( x i ) SEQUENCE DESCRIPTION: SEQ ID NO:109:

```
Leu Cys Ala Ser Ser Asp Ser Pro Ser Gly Gln Glu Thr Gln Tyr Phe
1               5                   10                  15

Gly Pro Gly Thr Arg Leu Thr Val Leu Glu Asp Leu Lys Asn
            20                  25                  30
```

( 2 ) INFORMATION FOR SEQ ID NO:110:

: ( i ) SEQUENCE CHARACTERISTICS:
:: ( A ) LENGTH: 30 amino acids
:: ( B ) TYPE: amino acid
:: ( C ) STRANDEDNESS: single
:: ( D ) TOPOLOGY: linear : ( i i ) MOLECULE TYPE: peptide : ( x i ) SEQUENCE DESCRIPTION: SEQ ID NO:110:

```
Leu Cys Ala Ser Ser Arg Pro Gly Asn Ile Arg Glu Thr Gln Tyr Phe
1               5                   10                  15

Gly Pro Gly Thr Arg Leu Ser Val Leu Glu Asp Leu Asn Lys
            20                  25                  30
```

( 2 ) INFORMATION FOR SEQ ID NO:111:

: ( i ) SEQUENCE CHARACTERISTICS:
:: ( A ) LENGTH: 33 amino acids
:: ( B ) TYPE: amino acid
:: ( C ) STRANDEDNESS: single
:: ( D ) TOPOLOGY: linear : ( i i ) MOLECULE TYPE: peptide : ( x i ) SEQUENCE DESCRIPTION: SEQ ID NO:111:

```
Leu Cys Ala Ser Ser Arg Ser Gln Gly Ala Arg Thr Gly Ala Asn Val
1               5                   10                  15

Leu Thr Phe Gly Ala Gly Ser Arg Leu Thr Val Leu Glu Asp Leu Lys
            20                  25                  30

Asn
```

( 2 ) INFORMATION FOR SEQ ID NO:112:

: ( i ) SEQUENCE CHARACTERISTICS:
:: ( A ) LENGTH: 29 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:112:

| Leu | Cys | Ala | Ser | Ser | Asp | Ala | Gly | Tyr | Asn | Ser | Pro | Leu | His | Phe | Gly |
|---|---|---|---|---|---|---|---|---|---|---|---|---|---|---|---|
| 1 |  |  |  | 5 |  |  |  |  | 10 |  |  |  |  | 15 |  |

| Asn | Gly | Thr | Arg | Leu | Thr | Val | Thr | Glu | Asp | Leu | Asn | Lys |
|---|---|---|---|---|---|---|---|---|---|---|---|---|
|  |  |  | 20 |  |  |  |  | 25 |  |  |  |  |

(2) INFORMATION FOR SEQ ID NO:113:

(i) SEQUENCE CHARACTERISTICS:
    (A) LENGTH: 30 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:113:

| Leu | Cys | Ala | Ser | Ser | Tyr | Arg | Thr | Gln | Leu | Asn | Ser | Pro | Leu | His | Phe |
|---|---|---|---|---|---|---|---|---|---|---|---|---|---|---|---|
| 1 |  |  |  | 5 |  |  |  |  | 10 |  |  |  |  | 15 |  |

| Gly | Asn | Gly | Thr | Arg | Leu | Thr | Val | Thr | Glu | Asp | Leu | Asn | Lys |
|---|---|---|---|---|---|---|---|---|---|---|---|---|---|
|  |  |  | 20 |  |  |  |  | 25 |  |  |  | 30 |  |

(2) INFORMATION FOR SEQ ID NO:114:

(i) SEQUENCE CHARACTERISTICS:
    (A) LENGTH: 32 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:114:

| Leu | Cys | Ala | Ser | Ser | Leu | Glu | His | Arg | Pro | Thr | Ala | Lys | Asn | Ile | Gln |
|---|---|---|---|---|---|---|---|---|---|---|---|---|---|---|---|
| 1 |  |  |  | 5 |  |  |  |  | 10 |  |  |  |  | 15 |  |

| Tyr | Phe | Gly | Ala | Gly | Thr | Arg | Leu | Ser | Val | Leu | Glu | Lys | Leu | Lys | Asn |
|---|---|---|---|---|---|---|---|---|---|---|---|---|---|---|---|
|  |  |  | 20 |  |  |  |  | 25 |  |  |  |  | 30 |  |  |

(2) INFORMATION FOR SEQ ID NO:115:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:115:

| Leu | Cys | Ala | Ser | Ser | Pro | Glu | Arg | Gly | Ala | Asn | Val | Leu | Thr | Phe | Gly |
|---|---|---|---|---|---|---|---|---|---|---|---|---|---|---|---|
| 1 |  |  |  | 5 |  |  |  |  | 10 |  |  |  |  | 15 |  |

| Ala | Gly | Ser | Arg | Leu | Thr | Val | Leu | Glu | Asp | Leu | Lys | Asn |
|---|---|---|---|---|---|---|---|---|---|---|---|---|
|  |  |  | 20 |  |  |  |  | 25 |  |  |  |  |

(2) INFORMATION FOR SEQ ID NO:116:

(i) SEQUENCE CHARACTERISTICS:
    (A) LENGTH: 28 amino acids
    (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO:116:

```
Leu Cys Ala Ser Ser Gln Glu Ala Ser Tyr Glu Gln Tyr Phe Gly Pro
1               5                   10                  15
Gly Thr Arg Leu Thr Val Thr Glu Lys Leu Lys Asn
            20                  25
```

( 2 ) INFORMATION FOR SEQ ID NO:117:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:117:

```
Leu Cys Ala Ser Arg Leu Val Arg Asp Leu Ser His Glu Gln Tyr Phe
1               5                   10                  15
Gly Pro Ser Thr Arg Leu Thr Val Thr Glu Asp Leu Lys Asn
                20                  25                  30
```

( 2 ) INFORMATION FOR SEQ ID NO:118:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:118:

AGCAGCCTAC GCGGGGCCAA C         21

( 2 ) INFORMATION FOR SEQ ID NO:119:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:119:

AGCAGCTTAC GCGGGACACC C         21

( 2 ) INFORMATION FOR SEQ ID NO:120:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:120:

AGCAGCTTGC GCTTGGCTAA T         21

( 2 ) INFORMATION FOR SEQ ID NO:121:

( i ) SEQUENCE CHARACTERISTICS:
( A ) LENGTH: 21 base pairs
( B ) TYPE: nucleic acid ( C ) STRANDEDNESS: single
                ( D ) TOPOLOGY: linear ( i i ) MOLECULE TYPE: cDNA ( x i ) SEQUENCE DESCRIPTION: SEQ ID NO:121:

AGCCAGTTGC GCTTGGCTAA T                                    21

( 2 ) INFORMATION FOR SEQ ID NO:122:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:122:

AGCAGCCAGT TGCGCTTGGC TAAT                                 24

( 2 ) INFORMATION FOR SEQ ID NO:123:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:123:

AGCAGCTTGG ATCGCTTGTA TAAT                                 24

( 2 ) INFORMATION FOR SEQ ID NO:124:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:124:

AGCACGTTGC GCTTGGGT                                        18

( 2 ) INFORMATION FOR SEQ ID NO:125:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:125:

AGCAGCCTAC GGGGGGCCAA C                                    21

( 2 ) INFORMATION FOR SEQ ID NO:126:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:126:

AGCAGCCTAC GGGGGGCCAA C  21

( 2 ) INFORMATION FOR SEQ ID NO:127:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:127:

ACGACGTTGA GGGGGGCGCT A  21

( 2 ) INFORMATION FOR SEQ ID NO:128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:128:

AGCAGCCTCA GGGGG  15

( 2 ) INFORMATION FOR SEQ ID NO:129:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:129:

AGCAGCATAA GGGGAAGC  18

( 2 ) INFORMATION FOR SEQ ID NO:130:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:130:

AGCAGCATCG TCAGGGGATC G  21

( 2 ) INFORMATION FOR SEQ ID NO:131:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:131:

AGCAGTTTAA GGGCGGGA  18

( 2 ) INFORMATION FOR SEQ ID NO:132:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:132:

AGCAGCCTCC GGGACTTT         18

( 2 ) INFORMATION FOR SEQ ID NO:133:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:133:

AGCAGCTTGG GAGGGGTACC CTAT         24

( 2 ) INFORMATION FOR SEQ ID NO:134:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:134:

AGCAGCTTGG GAGGGTCCGA AGAG         24

( 2 ) INFORMATION FOR SEQ ID NO:135:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:135:

AGCAGCTTGG GAGGGTCCGA AGAG         24

( 2 ) INFORMATION FOR SEQ ID NO:136:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:136:

AGCAGCTTGG GAGGGTCCGT TGAG         24

( 2 ) INFORMATION FOR SEQ ID NO:137:

( i ) SEQUENCE CHARACTERISTICS:
        ( A ) LENGTH: 18 base pairs
        ( B ) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:137:

AGCAGCCTGG GGGGCGAA 18

(2) INFORMATION FOR SEQ ID NO:138:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

Ser Ser Leu Arg Gly Ala Asn
1               5

(2) INFORMATION FOR SEQ ID NO:139:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

Ser Leu Arg Gly Thr Pro
1               5

(2) INFORMATION FOR SEQ ID NO:140:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

Ser Ser Leu Arg Leu Ala Asn
1               5

(2) INFORMATION FOR SEQ ID NO:141:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

Ser Gln Leu Arg Leu Ala
1               5

(2) INFORMATION FOR SEQ ID NO:142:

(i) SEQUENCE CHARACTERISTICS:
        (A) LENGTH: 7 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:142:

Ser Ser Gln Leu Arg Leu Ala
1               5

( 2 ) INFORMATION FOR SEQ ID NO:143:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:143:

Ser Ser Leu Asp Arg Leu Ala
1               5

( 2 ) INFORMATION FOR SEQ ID NO:144:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:144:

Ser Thr Leu Arg Leu Gly
1               5

( 2 ) INFORMATION FOR SEQ ID NO:145:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:145:

Ser Ser Leu Arg Gly Ala Asn
1               5

( 2 ) INFORMATION FOR SEQ ID NO:146:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:146:

Ser Ser Leu Arg Gly Ala Asn
1               5

( 2 ) INFORMATION FOR SEQ ID NO:147:

( i ) SEQUENCE CHARACTERISTICS:
( A ) LENGTH: 7 amino acids
( B ) TYPE: amino acid
( C ) STRANDEDNESS: single ( D ) TOPOLOGY: linear ( i i ) MOLECULE TYPE: peptide ( x i ) SEQUENCE DESCRIPTION: SEQ ID NO:147:

Ser Ser Leu Arg Gly Ala Leu
1               5

( 2 ) INFORMATION FOR SEQ ID NO:148:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:148:

Ser Ser Leu Arg Gly
1               5

( 2 ) INFORMATION FOR SEQ ID NO:149:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:149:

Ser Ser Ile Arg Gly Ser
1               5

( 2 ) INFORMATION FOR SEQ ID NO:150:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:150:

Ser Ser Ile Val Arg Gly Ser
1               5

( 2 ) INFORMATION FOR SEQ ID NO:151:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:151:

Ser Ser Leu Arg Ala Gly
1               5

( 2 ) INFORMATION FOR SEQ ID NO:152:

( i ) SEQUENCE CHARACTERISTICS:
( A ) LENGTH: 6 amino acids
( B ) TYPE: amino acid
( C ) STRANDEDNESS: single ( D ) TOPOLOGY: linear ( i i ) MOLECULE TYPE: peptide ( x i ) SEQUENCE DESCRIPTION: SEQ ID NO:152:

Ser Ser Leu Arg Asp Phe
1               5

( 2 ) INFORMATION FOR SEQ ID NO:153:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:153:

Ser Ser Leu Gly Gly Val Pro Tyr
1               5

( 2 ) INFORMATION FOR SEQ ID NO:154:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:154:

Ser Ser Leu Gly Gly Ser Glu Glu
1               5

( 2 ) INFORMATION FOR SEQ ID NO:155:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:155:

Ser Ser Leu Gly Gly Ser Glu Glu
1               5

( 2 ) INFORMATION FOR SEQ ID NO:156:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:156:

Ser Ser Leu Gly Gly Ser Val Glu
1               5

( 2 ) INFORMATION FOR SEQ ID NO:157:

( i ) SEQUENCE CHARACTERISTICS:
( A ) LENGTH: 6 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:157:

Ser Ser Leu Gly Gly Glu
1               5

T-CELL RECEPTOR VARIBLE TRANSCRIPTS AS DISEASE RELATED MARKERS

CROSS-REFERENCE TO RELATED APPLICATIONS

This application is a continuation of U.S. application Ser. No. 07/877,444, filed Apr. 30, 1992, now abandoned, which is a continuation-in-part of application Ser. No. 07/517,245 filed May 1, 1990, now abandoned and International Application Ser. No. PCT/US91/02991 filed May 1, 1991 now WO 92/21 367.

ACKNOWLEDGEMENTS

This invention was supported in parts by grants from NIH. The U.S. Government may have rights in this invention.

INTRODUCTION

1. Technical Field

The field of the subject invention is diagnosis and treatment of diseases, particularly autoimmune and cancer.

2. Background

Autoimmune diseases are a result of a failure of the immune system to avoid recognition of self. The attack by the immune system of host cells can result in a large number of disorders, including such neural diseases as multiple sclerosis and myasthenia gravis diseases of the joints, such as rheumatoid arthritis, attacks on nucleic acids, as observed with systemic lupus erythematosus and such other diseases associated with various organs, as psoriasis, juvenile onset diabetes, Sjogren's disease, and thyroid disease. These diseases can have a variety of symptoms, which can vary from minor and irritating to life-threatening.

Despite the extensive research efforts that have been involved with elucidating the basis for these diseases, the diseases for the most part have been recalcitrant to an understanding of their etiology in the development of therapeutic modes. Many of the diseases are believed to be associated with lymphocytic involvement, which can result in attack and degradation of proteins, cytotoxicity, and the like.

In the case of cancer, tumor infiltrating lymphocytes (TIL) are believed to be part of the body's defense mechanism to destroy the tumor. Efforts have been made to expand T-cells found in tumor tissue and return the culture expanded cells to the host.

The complexity of the immune system has been a daunting barrier to an understanding of the autoimmune diseases and the immune response to neoproliferative diseases. In attempting to understand the mechanisms involved with the immunological response, there is substantial interest in understanding in what manner the system degenerates to attack self. By understanding the relationships between the components of the immune system, the manner in which the immune system distinguishes between self and non-self, and the components the immune system associated with a particular disease, ways may be developed to diagnose individuals who may be susceptible to autoimmune diseases and provide therapies to protect such susceptible individuals from autoimmune disease during its onset and during its progress or to treat individuals with specific T-cells.

Relevant Literature

Multiple sclerosis (MS) is an inflammatory disease of the central nervous system characterized by myelin destruction (McFarlin and McFarland, *New Engl. J. Med.* 307:1183–1251 (1982)). At the site of demyelination, depletion of oligodendroglia cells and proliferation of astrocytes is usually observed. Raine and Traugott, Immunoregulatory Processes in Experimental Allergic Encephalomyelitis and Multiple Sclerosis, Elsevier, New York, 151–212 (1984); Prineas and Wright, *Lab. Invest* 38:409–421 (1978). There is an accumulation of morphologically identifiable macrophages, plasma cells and T lymphocytes, characteristic of an inflammatory response in the brain. Prineas, Handbook of Clinical Neurology, 3, Elsevier, New York, (1985) pp. 213–257. MHC Class II, positive antigen presenting cells and activated T-cells secreting various cytokines are present. Woodroofe et al., *J. Neurol. Sci.* 74, 135–152 (1986); Hafler and Weiner, *Ann. Neurol.* 22, 89–93 (1987); Hafler and Weiner, *Immunol. Rev.* 100, 307–332 (1987); Hoffman, *J. Exp. Med.* 170, 607–612 (1989). Several lines of evidence suggest that T lymphocytes migrate from the peripheral blood through the CNS compartment and participate directly in the promotion of brain lesions. Hoffman et al., *J. Immunol.* 136, 3239–3245 (1966); Traugott, *J. Neuroimmunol.* 4, 201–221 (1985). In studies of MS plaque tissue with monoclonal antibodies, it has been shown that the majority of T-cells have the helper inducer CD4 positive phenotype. Sobel et al., *J. Exp. Med.* 167, 1313–1322 (1988). Also, by restriction fragment length polymorphism analysis, T-cell receptor $V\alpha$ and $V\beta$ genes have been shown to contribute to the genetic control of susceptibility to this disease. Beall et al., *J. Neuroimmunol.* 21, 59–66 (1989); Seboun et al., *Cell* 57, 1095–1100 (1989); Oksenberg et al., *Proc. Natl. Acad. Sci. USA* 86, 988–992 (1989) describe the use of TIL cells in the treatment of tumors (Barth et al., *J. Immunol.* 144, 1531 (1990)).

HLA-DR2Dw2 is associated with increased susceptibility to MS. Terasaki et al. *Science* 193:1245–1247 (1976). Susceptibility to MS has been associated with certain MHC Class II genes. Oksenberg and Steinman, Current Opinion in Immunology 2:619–621 (1990). At the cellular level, oligoclonality of T-cells has been described in the cerebrospinal fluid (CSF) of MS patients. Lee et al., *Ann. Neurol.* 29:33–40 (1991). Oksenberg et al., *Nature* 345:344–346 (1990) describes the use of PCR to amplify TCR $V\alpha$ sequences from transcripts derived from MS brain lesions. Wucherpfennig et al. *Science* 248:1016–1019 (1990) and Ota et al., *Nature* 346:183 (1990) report studies of T-cell clones in man that recognize myelin basic protein.

SUMMARY OF THE INVENTION

The relationship of particular sequences of the $V\alpha$ and/or $V\beta$ subunits of the helper T-cell receptor is established by identifying invasive T-cells in tissue from autoimmune or neoplastic lesions. The particular variable regions may be identified from germline rearrangement, mRNA or the T-cell receptor subunit sequences. The oligoclonal regions of the T-cell receptor ("TcR") or the cells having such regions are then used for therapeutic applications for the treatment of the diseases. With disease causing T-cells, the peptides may be used by themselves to block binding, for the formation of antibodies, or the preparation of cytotoxic molecules specific for the target T-cell. Sequences based on motifs associated with the disease are provided for diagnosis and therapy.

In conjunction with the restricted repertoire of the TcR, the MHC phenotype is also relevant to susceptibility to particular autoimmune and neoplastic diseases. By screening for the presence of the susceptible phenotype, counseling and monitoring can be provided to minimize the occurrence and/or severity of the disease.

DESCRIPTION OF THE SPECIFIC EMBODIMENTS

Methods and compositions are provided for determining T-cell receptor variable regions related to autoimmune diseases. Also specific MHC profiles may be identified associated with specific autoimmune diseases, which will provide for monitoring of such patients to identify initiation of symptoms of such disease.

For autoimmune disease, by identifying specific T-cell receptor (TcR) variable regions associated with the disease, therapies may be employed to inhibit the attack of the T-cells having such variable regions on the target cells or proteins. The therapies may involve ablation of T-cells carrying the particular variable regions, administration of compounds which inhibit binding of the T-cell receptor to the target cell, or prevention of the degenerative effects of the binding of the T-cell to the target cell or protein. For neoproliferative diseases, the T-cells having the appropriate T-cell receptor may be concentrated and expanded and returned to the host.

The T-cell receptor has two subunits involved in binding, either α and β, or γ and δ. The variable regions associated with the subunits have a similar organization to those of the immunoglobulins, the β and γ subunits having a variable region which comprises exons associated with the V, D and J regions, while the α and δ subunits comprise exons associated with the V and J regions. By rearrangement of germline DNA, the exons are joined to the constant or conserved region and by subsequent splicing of the messenger RNA, an open reading frame is achieved which encodes the subunit. Depending upon the particular genetic inheritance of the host, the spectrum of the variable region loci of an individual will be different from other individuals. In addition, not all variable region exons present may rearrange to form a functional T-cell receptor subunit.

For some autoimmune diseases, one may wish to distinguish between a lesion associated with a chronic condition or an acute condition. For example, for multiple sclerosis, the chronic condition is exemplified by the presence of large numbers of macrophages and relatively low number of T-cells in comparison to acute phase which has lower levels of macrophages and higher levels of T-cells. The cells may be identified in accordance with conventional histocytochemistry techniques, using antibodies to surface markers, as appropriate.

By determining the loci which are rearranged to form functional variable regions, which variable regions are associated with autoimmune lesions, one can diagnose the nature of an autoimmune disease, establish the existence of a chronic episode, and treat the disease, prophylactically or therapeutically, by inhibiting the degenerative effect of the T-cells. By determining the loci which are rearranged to form functional variable regions effective against tumors, these cells may be used to combat the tumor.

T-cell receptors may be divided into two categories: the CD4 helper-inducer T-cell receptors, which T-cell receptors bind to Class II MHC; and the CD8 suppressor-cytotoxic T-cell receptors, which T-cell receptors bind to Class I MHC. For the most part, the T-cells associated with such diseases as multiple sclerosis are the CD4 positive phenotype, though CD8 can also play a role.

The autoimmune diseases of significant prevalence include multiple sclerosis, associated with destruction of myelin and glial cells, rheumatoid arthritis, associated with joint lesions, systemic lupus erythematosus (SLE), associated with the deposition of autoantibodies and immune complexes, psoriasis, pemphigus vulgaris, juvenile onset diabetes, associated with destruction of beta cells in islets of Langerhans, Sjogren's disease, thyroid disease, Hashimoto's thyroiditis, myasthenia gravis, as well as many others.

The variable (V) loci by themselves or in conjunction with the J loci of the T-cell receptors of T-cells found at the site of the lesion may be identified in a number of different ways. Particularly, the lesion or plaque is isolated and total RNA, from which cDNA may be prepared, or DNA is prepared according to standard procedures. To provide for more accurate results, the cDNA is amplified by any convenient technique, such as the polymerase chain reaction (PCR), cloning, or the like. In the case of the polymerase chain reaction, primers are employed which will identify the particular variable region which either has been expressed as identified by cDNA, or has been rearranged, so as to be associated with a J and C region.

Primers may be selected in accordance with the known sequences of conserved regions of the T-cell receptor subunits. It is found, that there will usually be 1 and no more than about 7, usually not more than about 5, generally only about 3 common, variable regions of the T-cell receptor subunits associated with the lesions. Therefore, with neural disorders, where the tissue is available from a deceased or from a biopsy having the particular disorder, one may relate the presence of T-cells in the lesions to the disease and, further, relate the particular V regions and J regions associated with the T-cells present in the lesion with the MHC antigen type of the deceased. In this manner, one may provide for identification of the variable regions of humans suffering from the disease with the MHC type and be able to treat the disease accordingly. With genomic DNA, one would establish the presence of the rearrangement in the DNA by having primers which relate to substantially conserved regions of the variable region and the joining of the constant region, either coding or non-coding regions. Alternatively, by cloning, one could sequence the DNA and establish the identity of the variable region. Isolation of mRNA from the tissue in question, reverse transcription to cDNA and then amplification and identification of the rearranged V-C product will also define the disease related marker. Similarly, with neoproliferative tissue, the tissue may be isolated and the T-cells effective for combatting the neoproliferative cells identified.

Instead of the nucleic acid as the basis for the diagnosis, by having a battery of monoclonal antibodies, various techniques may be employed for identifying the binding of the antibody to the T-cells. Thus, flow cytometry, e.g. a FACS scan, may be employed, where the antibodies are labeled with a fluorescer and those T-cells to which the antibodies bind would then identify the particular variable region.

A 100% correlation is normally not to be expected, not will it be necessarily achieved. It will usually be satisfactory that in at least 60%, preferably 70%, of the hosts positive for the disease, the variable region locus associated with the disease is present in host T-cells, particularly in rearranged form. Similarly, in fewer than about 50%, preferably in fewer than about 30% of the hosts which do not present the symptoms of the disease, the rearranged variable region is absent. These percentages should be based upon a statistically significant number of hosts.

Depending upon the particular disease, various tissues may be employed for identifying the T-cells. For neural diseases such as multiple sclerosis, brain plaques or cerebrospinal fluid may be employed as a source of the T-cells. Similarly, for myasthenia gravis, muscle, thymus tissue or T-cells responsive to acetylcholine receptor may be employed. For rheumatoid arthritis, the synovium may be employed. For other diseases such as thyroiditis, or Grave's disease, thyroid tissue, or in systemic lupus erythematosus, kidney tissue may be employed as the source of T-cells.

Once the rearranged variable region(s) are established, one may then identify T-cell variable region allele(s) or T-cell receptors in a host, in association with the HLA or MHC restriction, as indicative of the propensity for the disease or the existence of the disease or the neoproliferative cell responsive T-cells. Where it appears that the disease is associated with one or a plurality of T-cells, the presence of one or more of the T-cell receptors having the rearranged variable regions associated with the disease will indicate the greater or lesser likelihood for the occurrence of the disease.

For diagnosis of autoimmune diseases, either the nucleic acid or antigen may be detected. For nucleic acid detection, DNA or RNA in cells may be isolated by any convenient means and by employing appropriate probes, in conjunction with techniques, such as Southern transfer, dot-blots, or the like, the presence of the rearranged V region may be detected. Depending upon the nature of the disease, there may be an opportunity for prophylactic intervention to reduce the potential for the disease occurring.

If one wished to determine the number of cells which are expressing the T-cell receptors associated with the disease, this can be achieved in a number of ways. The messenger RNA may be isolated from T-cells and probed with an appropriate probe for the V gene region. By employing Northern techniques, one can detect the presence of the messenger encoding the T-cell receptor and obtain a qualitative value for the amount of T-cell receptor being expressed containing the particular V region gene. Alternatively, one may prepare cDNA from the messenger and using the polymerase chain reaction, amplify the amount of messenger and determine the number of T-cells expressing the particular variable region in this manner.

More conveniently, one may use antibodies as described previously which are specific for the V region and/or the J region alleles or potentially the combination V-J for the α subunit. In this way, one may detect the V region and the J region, With the β subunit, intervention of the D region makes it unlikely to find a antibody which would be specific for the VDJ sequence, but the V and/or J region may be detected individually.

Antibodies may be prepared in accordance with conventional ways, particularly employing the monoclonal antibody techniques as described, for example in U.S. Pat. Nos. 4,690,893; 4,713,325; 4,714,681; 4,716,111; and 4,720,459.

Any of a number of techniques may be employed for identifying the presence of a T-cell receptor binding to the particular monoclonal antibody or anti-serum. A wide variety of labels have been used for detection, such as particles, enzymes, chromophores, fluorophores, chemiluminescence, and the like. Any particular label or technique which is employed is not critical to this invention and any convenient technique may be employed. The techniques may be either competitive or non-competitive methodologies, including sandwich methodologies. The cells will usually be lysed to provide membrane-free proteins in accordance with conventional techniques. Cellular debris may be removed and the protein extracted and harvested. Alternatively, intact cells may be employed and detected by fluorescence activated cell sorting or the like.

For therapeutic purposes, there may be an interest in using human antibodies. Normally, one will not be permitted to immunize a human host with the T-cell receptor or fragment thereof to activate T-cells specific for the sequence of interest. However, there are alternatives, in that mice or other lower mammals may be immunized, and the genes encoding the variable regions of the antibodies specific for the T-cell region of interest isolated and manipulated by joining to an appropriate human constant region, and optionally, the complementary determining regions (CDR) used to replace the CDRs of a human antibody by genetic engineering. The resulting chimeric construct, comprising a lower mammal variable region or CDRs and a human constant region may then be transformed into a microorganism or mammalian host cell in culture, particularly a lymphocyte, and the hybrid antibodies expressed. Of particular interest would be IgG constant regions. See, for example, EPA 173,494 . Also recent techniques suggest random association of immunoglobulin genes from a human host for expression in a non-human cell host e.g. prokaryotic, and screening for affinity.

In some instances, it may be satisfactory to use mouse antibodies, where tolerance can be achieved or some degree of immune suppression may be involved. Immune suppression may be achieved with cyclosporin, irradiation, anti-leu3 (anti-CD4) (U.S. Pat. No. 4,681,760), or the like.

The antibodies may be used in a variety of ways, for example, for inhibiting binding between the T-cell and the target cell, for killing of T-cells, or for isolating the T-cells. In the first situation, the entire antibody may be administered, or Fab fragments, or even only the Fv region. By removing all or a portion of the constant region, there may be a reduction in the immune response. For selectively killing the T-cells carrying the particular V region, one may use a variety of immunotoxins, which may include the antibody or specific binding fragment thereof, bonded to all or a portion of a plant toxin, such as ricin, abrin, etc., or diphtheria toxin. By employing an appropriate antibody isotype, e.g., IgM or $IgG_3$, the complement cascade may be enlisted. Alternatively, a radioactive substituent may be used which provides for a lethal dosage upon binding of the antibody to the host cell. Another choice is to use an antibody or fragment thereof conjugated with a cytolytic agent for specific elimination of the undesired T-cells. Finally, the T-cell can be removed by extracorporeal means, such as plasmapheresis, where the plasma may be passed through or over antibodies bound to a support, with the undesired T-cells being selectively removed.

For therapeutic purposes, the antibody may be formulated with conventional pharmaceutically or pharmacologically acceptable vehicles for administration, conveniently by injection. Vehicles include deionized water, saline, phosphate-buffered saline, Ringer's solution, dextrose solution, Hank's solution, etc. Other additives may include additives to provide isotonicity, buffers, preservatives, and the like. The antibody or derivative thereof will usually be formulated in purified form at concentrations in the range of about 0.05 to 10 μg/ml. The antibody may be administered parenterally, typically intravenously or intramuscularly, as a bolus, intermittently or in a continuous regimen.

Desirably, the dose should deplete or at least bind about 75% of the undesired T-cells, preferably at least about 90%. Typical doses for adult humans will be in a range of about 10 to 100 mg. Doses for children or other animal species may be extrapolated from the adult human dose based on relative body weight.

Instead of antibodies, oligopeptides may be employed, having the same or substantially the same sequence as the oligopeptide sequence identified as being diagnostic of the autoimmune disease. These sequences will be oligopeptides of at least 8, usually at least 10 more usually at least 12, and preferably at least 18 amino acids, and generally not more than about 60 amino acids, usually not more than about 50 amino acids, of the T-cell receptor subunit chain. While the entire subunit(s) may be employed, usually, not more than about 50 number % of the amino acids will be employed, particularly excluding the conserved or constant region. All or at least a portion of the variable region, capable of binding to the target protein (the protein recognized by the T-cell receptor) and/or MHC antigen, will be present. The MHC antigen may be by itself or bound to a fragment of the target protein, which fragment will normally include the particular locus associated with the disease.

Of particular interest, is the demonstration that the variable rearrangements of T-cells associated with specific sites of autoimmune disease, have a restricted repertoire, so that a relatively small number of T-cell variable regions of both the α and β subunits will be observed. Furthermore, as will be discussed below, a limited repertoire of MHC type will be associated with the disease and as to these repertoires, there will generally be a restricted repertoire of T-cell receptor variable regions.

In particular, with MS patients it is found in the brain, particularly in the plaques associated with the disease, that T-cells may be isolated which have rearranged germline DNA to provide for expression of the T-cell receptor. This may be contrasted with brains of normal healthy individuals, where the T-cells found in the brain have unrearranged germline DNA.

By identifying a particular Class II haplotype or molecular phenotype, one can then identify particular Vα and Vβ variable regions associated with an autoimmune disease. Once the autoimmune associated T-cell receptor or variable regions are identified, one may than use the various therapies which are described in the subject application for prophylaxis or treatment.

As previously indicated, of particular interest are specific V regions and J regions of both the α and β chains of the T-cell receptor. For sequences of human and mouse V regions, see Concannon, et al., Proc. Natl. Acad. Sci. USA 83:6598–6602 (1986). Of the regions of interest of CD4 T-cell associated with multiple sclerosis, among Vα families are 8–10, 12 and 16, particularly 10. Other regions of interest include 1, 5 and 7.

Of the J regions, of particular interest are Jα regions, more particularly the Jα region (SEQ ID NO:1) GGGTACCGAGATGACGAACCCACCTTTGGGACAGGCACTCAGCTAAAAGTGCAACTC.

Of the Vβ regions, are the families 5, 6, 7 and 12 more particularly 5 and 6, and of the Vβ 5 family, particularly 5.1 and 5.2.

In addition, certain amino acid sequence motifs are seen in the CDR3 region of the TCR. The sequences appear more frequently than would be expected and follow the sequence (SEQ ID NO:2) LCAS(S) (where the parentheses indicate the optional presence of the amino acid), particularly LCASS. The next amino acid will be one having a long chain, neutral, preferably hydrocarbon, such as L, I and V, or Q, particularly L. The next amino acid may be neutral or charged positively or negatively charged, may be short (2–4 carbon atoms) or long (5 to 6 carbon atoms), and may include G, A, P, L, I or V, as well as D, E, K, and R, particularly G, A, V, D and R, more particularly R and G, which are involved with sequences specific for the MBP sequence 87 to 106. The next amino acid will frequently be G, A or S, so that the motif will be L-X-(G, A or S), particularly (G). An alternative motif is P following LCAS (S), where the next amino acid is PT.

These peptides may be isolated free of flanking amino acids or may include up to a total of about 20 flanking amino acids. Alternatively, flanking regions may be provided which are not naturally occurring sequences. The peptides may be modified and used as described previously.

For the most part, the sequence will be derived from Jβ 1 and 2, more particularly 1.2, 1.6, 2.1, 2.3, 2.5, 2.6 and 2.7.

This same approach may be used to identify the rearrangement and expression of T-cell receptor subunits, both for restriction as to Class I and II MHC, to identify sequences associated with pathogenesis.

The presence of pathogenic T-cells may be detected with various probes, such as AGC CTA CGC; AGC TTG CGC; AGC CTG CGG; TTG CGC; and (SEQ ID NO:3) AGC CTA CGC AGC TTG CGC AGC CTG CGG TTG CGC (specific for LRGA). The probes may be as few as 6 nucleotides and as many as 30 nucleotides, usually being not more than about 31 nucleotides.

The peptides may serve as vaccines, to obtain an immune response, to ablate the pathgenic T-cells. Immune responses may be achieved in accordance with conventional ways. The peptides may be conjugated to an immunoassay, introduced into a viral vector so as to be fused to the envelope or capsid protein, fused to proteins using recombinant technology, and the like.

The oligopeptide may be joined to other peptides, proteins, or polyalkyleneoxy compounds for a variety of reasons, such as to provide for enhanced stability, toleration, ease of preparation or purification, or the like. The subject peptides may be used to inhibit the binding of the T-cell receptor to the target peptide.

The peptide may be formulated in substantially the same manner as described for the antibodies. The amount of the active ingredient administered will vary widely depending on the particular composition, the particular host, the number and frequency of administrations, the manner of administration, etc. Usually there will be from about 0.01 to 10 µg/kg of host, more usually from about 0.05 to 5 µg/kg of host, where the concentration may range from about 10 µg/ml to about 1 mg/ml.

The manner of administration may vary widely, depending upon the formulation and nature of the active ingredient. Administration may be parenteral, intravascular, peritoneally, subcutaneous, oral, etc., may employ catheters, pumps, constant diffusion membranes, etc.

The oligopeptides may be prepared in a variety of ways, conveniently, in accordance with conventional synthetic procedures. Where larger sequences are involved, such as 30 amino acids or more, recombinant DNA techniques may be employed, where the gene may be synthesized in accordance with conventional ways, such as commercially available DNA synthesizers, expanded employing the polymerase chain reaction, and then inserted into an appropriate vector having the necessary transcriptional and translational initiation and termination regions. The resulting vector is then transformed into a host in which the expression vector is replicated and functional expression is obtained. The product may be secreted and harvested from the medium or when not secreted and retained cytoplasmically, the cells are harvested, lysed, and the desired protein isolated and purified in accordance with conventional ways.

Instead of the oligopeptide, anti-idiotype antibodies may be employed. By preparing a monoclonal antibody to the idiotype of the antibody to the subject oligopeptide, the anti-idiotype may mimic the oligopeptide and serve to compete for the MHC with the T-cell receptor for the MHC antigen. The anti-idiotype may provide greater stability on administration, as well as other advantages.

T-cells can be inhibited from reacting with MHC antigens which may result in pathogenesis by employing ribozymes specific for one or both subunits of the T-cell receptor. For the Class I TcR, the ribozyme would be directed against the α-subunit, while for the Class II TcR, either the α- and/or the β-subunit could be the target. The ribozyme would comprise a sequence having complementarity to the sequence encoding the CDR3. Unnatural nucleotides may be used to enhance stability, such as the presence of thiolinkages or replacement of oxygen in the phosphate group with carbon groups or the like. Alternatively, antisense sequences could be used which were specific for the target subunits. Administration of the ribonucleotides would be in accordance with conventional means in relation to the transport of the ribonucleic acid across the blood-brain barrier.

The protective compositions may be used in vitro or in vivo by adding to groups of cells comprising lymphocytes and cells associated with the autoimmune disease or target protein. By adding the protective composition, usually a protein such as an antibody or peptide having the appropriate variable region sequence, one can prevent the destruction of the cells and/or target protein. Where cells are involved, the T-cells will be restricted by restricted by the major histocompatibility antigen of the target cells, with the target cells usually being syngeneic with the T-cells.

In addition to the compositions of this inventions, other compositions may be employed to enhance protection. These compositions may comprise oligopeptides, one or more different oligopeptides, comprising the following sequence: charged amino acid, two hydrophobic amino acids, and at least one of the next two amino acids being a polar amino acid, where the charged or polar amino acid may be substituted by glycine, usually not more than one being substituted by glycine. The charged amino acids are aspartic acid, glutamic acid, lysine, arginine, and histidine (D, E, K, R, H). The hydrophobic amino acids are alanine, proline, valine, leucine, isoleucine, methionine, phenylalanine, tryptophan, and tyrosine, that is both the aliphatic and aromatic neutral or substantially neutral amino acids having not more than one heteroatom, e.g., chalcogen, on the side chain (A, P, V, L, I, M, F, W, and Y). The polar amino acids will be the charged amino acids, as well as serine, threonine, asparagine, and glutamine (S, T, N, and Q).

The motif sequence may be part of a sequence of an immunogen of interest, associated with an autoimmune disease, e.g., myelin and multiple sclerosis, there usually being more than one partial sequence in the immunogen comprising the subject motif. The oligopeptide comprising the subject motif may be from any site of the immunogen sequence, that is N-terminal or C-terminal proximal or central, where the oligopeptide sequence will normally be substantially homologous with from 9-15 amino acids of the immunogen sequence, although longer sequences may also be employed. Usually, the difference in homology between the natural sequence and the oligopeptide which is employed will be not more than two lesions, more usually not more than 1 lesion, which may be insertions, deletions, or conservative or non-conservative substitutions.

Usually, the motif sequence present in the oligopeptide will be at other than the C-terminus of the oligopeptide, desirably being at the N-terminus and not closer to the C-terminus than the center of the sequence, where the second, third, or fourth amino acid of the motif (depending upon whether there are four or five amino acids in the motif) is the central amino acid.

The compositions of this inventions will include usually at least one sequence of an immunogen of interest including the subject motif and may include two or more oligopeptide motifs containing sequences of from about 9-15 amino acids present in the immunogen, depending upon the number of motifs present in the immunogen. Thus, if there are a plurality of motifs present in the immunogen, all or fewer than all of the sequences including the motifs may be employed in a single composition. Usually, there will be not more than ten different motif comprising oligopeptides, more usually not more than about six different oligopeptides in the composition.

In preparing the subject compositions, one would select an immunogen related to the autoimmune disease of interest against which an immune response of a host is to be modulated. The oligopeptide may serve to tolerize the host to prevent immune attack against the endogenous protein or cell producing the endogenous protein.

The particular protein of interest will be screened for the presence of the subject motif and one or more sequences including the motif selected. Where the histocompatibility genotype (haplotype) of the intended recipient is known, one sequence may be preferred over another. However, where the haplotype is not known, or the composition may be administered to a number of different hosts, it will frequently be desirable to combine a number of the sequences as oligopeptides in the same composition. The oligopeptides may be present as the individual peptides, or may be joined together in a single sequence, with or without intervening bridges, where any bridges will be other than the naturally occurring intervening sequences of the immunogen. Desirably, any such sequence would have fewer than about 100 amino acids, more usually fewer than about 60 amino acids.

The subject oligopeptides may be modified in a variety of ways. For toleration, the subject peptides may be conjugated to syngeneic spleen cells, or be linked to an innocuous immunogen to which the host has been previously immunized, such as tetanus toxoid, bovine serum albumin, etc. Adjuvants are normally avoided.

Sequences which may be employed for toleration will be sequences from proteins endogenous to the host involved with autoimmune diseases, which include such proteins as the neurological proteins found in the peripheral nervous system (PNS) or the central nervous system (CNS) and the acetylcholine receptor (AChR). These proteins are designated as $P_o$ which is found in the PNS and CNS, P1, in myelin basic protein, the predominant CNS protein of myelin, P2, a predominant PNS myelin protein, PLP, a proteolipid protein, a PNS and CNS myelin constituent, and the acetylcholine receptor. P1 is involved in post-immunization encephalomyelitis and may be involved in multiple sclerosis. P2 is involved in post-immunization neuritis (Guillain-Barre syndrome) a major complication, for example, in the swine flu immunization program and the acetylcholine receptor is involved in myasthenia gravis and may play a role in post-immunization myositis. These protein fragments may be modified by one or more lesions to maintain the binding affinity for the MHC antigen while substantially reducing the binding affinity to the T-cell receptor.

Transplantation or MHC antigens have polymorphic regions, where the individual alleles are associated with specific hosts. For the most part, the host will be diploid and heterozygous, so that each host will have two haplotypes, meaning that there will be two different copies of a particular transplantation antigen type from the same locus, unless the host is homozygous at that particular locus. Therefore, as to an individual host or a plurality of hosts, mixtures of oligopeptides will usually be employed. The subject oligopeptides may be administered concurrently or consecutively with the oligopeptides of the T-cell receptor. The subject oligopeptides may be administered in a variety of ways, by themselves or in conjunction with various additives. Various carriers may be employed which are physiologically acceptable, such as water, alcohol, saline, phosphate buffered saline, sugar, mineral oil, etc. Other additives may also be included, as stabilizers, detergents, flavoring agents, thickeners, etc. The amount of active ingredient administered will vary widely depending upon the particular composition, the particular host, the number and frequency of administrations, the manner of administration, etc. Usually, there will be from about 0.01–10 µg/kg of host more usually from about 0.05–5 µg/kg of host, where the concentration may range from 10 µg/ml–1 mg/ml.

For identifying T-cells associated with combatting neoproliferative diseases, by identification of the variable region associated with such T-cells, tissue may be obtained by biopsy, surgical intervention or the like, the mRNA or DNA may be isolated from the tissue sample and in the case of mRNA, cDNA prepared in accordance with conventional ways. The DNA sample may then be assayed using a primer specific for the various Vα or Vβ regions to identify the predominant variable region associated with the disease. Once a number of patients have been screened, the likely variable region(s) associated with a particular tumor will have been identified. One may then use the affinity separations, e.g. panning, affinity chromatography, etc. for isolating the desired T-cells. The cells may then be expanded in culture using a conventional growth medium, with or without the addition of fetal calf serum, interleukins, e.g. IL-2, or the like. The cells may then be harvested after expansion by at least 100 and restored to the donor.

Alternatively, one may have a stored supply of T-cells of the appropriate variable region and either matched or unmatched as to MHC, particularly Class I. These cells may then be administered by injection into the neoproliferative tissue site, or into the blood stream. From $10^3$ to $10^9$ cells may be administered to a human host in a physiologically acceptable medium, the amount varying with the number of cells available, the manner of administration, the frequency of administration, and the like.

In addition to identifying T-cell variable regions associated with specific autoimmune diseases such as multiple sclerosis, one may in addition identify specific molecular phenotypes associated with susceptibility to autoimmune disease. The phrase "molecular phenotype" is used instead of the designation "haplotype" since in the absence of segregation analysis in families, it cannot be certain whether these genes are all in a cis configuration on a single chromosome. A phenotype associated with multiple sclerosis is DRB1 1501, DQA1 0102 and DQB1 0602. This phenotype may be further broken down into 1a, associated with DPB1 0401 and 1b 0402. This particular phenotype is associated with Vβ family rearrangements, particulary Vβ 5.1, 5.2 and 6.

By identifying MHC molecular phenotypes of individuals suffering an autoimmune disease, one can establish certain molecular phenotypes which provide for a susceptibility to the disease. In the case of multiple sclerosis one can look to see for rearrangement of T-cells and the prevalence of the various families and members of the families of the Vβ and Vα T-cell receptors. Once these are identified, one can use this information to ablate the T-cells associated with the disease. Thus, by isolating diseased tissue, e.g., plaques, and identifying T-cells having rearrangements, one can identify a family of Vβ and Vα regions which are associated with the disease, so that once the molecular phenotype has been identified as providing susceptibility to autoimmune disease one will also know which T-cells to ablate or target.

The upregulation of the MHC antigens on neural cells at lesions affords an opportunity to direct specifically various agents to the site of the lesion. Thus, one may use a variety of radionuclides, nmr agents, or other agents which provide a detectable signal for identifying the site of the lesion. The agent providing the signal may be joined to various carriers, such as antibodies for the MHC, or fragments of antibodies, e.g. Fab, Fv, etc., immunodominant sequences which are peptides of about 10, usually 12, amino acids or more, which have a high affinity for the MHC antigen. The presence of hematopoietic cells at the lesion, will further augment the presence of the agent at the lesion. The signal at the lesion should be greatly enhanced, as compared to other regions of the brain.

Besides diagnosis, one may use the selective presence of the MHC antigens for therapeutic purposes. Thus, one may direct various therapeutic agents, by conjugating the agent to the MHC antigen specific marker, by using the MHC antigen specific marker for directing therapeutic agent containing liposomes to the lesion site. Agents may include inhibitors of TNFα, downregulators of MHC antigen expression, e.g. β-interferon, TGF-β, and α-fetoprotein, peptides which block the MHC antigen-TcR interaction, inhibitors of generalized degradative pathways, such as reducing agents and superoxide dismutase for singlet oxygen, etc.

Since the disease results in some permeabilization of the blood-brain barrier, the opportunity to introduce drugs across the barrier is enhanced. One may still use injections at specific sites, permeabilizing agents, or employ naturally occurring transport mechanisms.

The various agents will be administered in accordance with their individual nature and in accordance with their purpose. Inert physiologically acceptable carriers may be employed, such as deionized water, saline, and the like. Concentrations and the use of other additives or components will be based on experience with like reagents and may be determined empirically.

The following examples are offered by way of illustration and not by of limitation.

EXPERIMENTAL

TcR Vα Expression in Brain Plaques of Multiple Sclerosis

Samples were taken from brain plaques of 3 patients with chronic progressive MS, and 3 controls (non MS). Total RNA and cDNA (from 5 µg RNA) were prepared according to standard procedures. cDNA was also prepared from 1 µg RNA isolated from a pool of peripheral blood lymphocytes from five different individuals, stimulated with 3 µg/ml of PHA. cDNAs were amplified by PCR for 40 cycles in the presence of 10 µCi of [$^{32}$ $^P$]dATP (Amersham). Samples were analyzed by gel electrophoresis with ethidium bromide to identify the specific fragment band. After separation, bands were excised and radioactivity was determined. Results are expressed in median cpm. All TcR 5' primers amplify TCR sequences from germ line DNA using a specific 3' Vα primer for each family. The following Tables 1 and 2 indicate the primers employed and the results. Table 1 provides the sequence of the primer used for the different T-cell receptor Vα idiotypes. The first column beginning from left to right indicates the idiotype Vα chain, the second column indicates the internal designation for the clone of the primer sequence, the third column indicates the primer nucleic acid sequence, and the fourth column indicates the T-cell receptor family which has the sequence in the α subunit. Table 2 provides in the horizontal row at the top, the particular idiotype. Two experiments were carried out with the same three MS patients and three controls, where the first vertical column beginning at the left indicates MS for the Multiple Sclerosis patients and C for the control patients. The results are reported as to cpm for radioactive cDNA resulting from the use of each of the primers in a polymerase chain reaction using radioactive nucleotide triphosphates. As is evident from the results, the Vα8, Vα9, Vα10, Vα12, and in one instance Vα16 showed cpm greater than background. A comparison is also provided with actin, using a primer for actin. The PBL(PHA) horizontal row is a pooled sample of cDNA of PHA (phytohemagglutinin) stimulated peripheral blood lymphocytes from five different individuals.

TABLE 1

T-cell Receptor α Primers.

| Primer | SEQ ID | Clone | Sequence | Family Members |
|---|---|---|---|---|
| Vα 1 | 4 | HAP 10 | 5'-TTGCCCTGAGAGATGCCAGAG-3' | 1.1, 1.2, 1.3 |
| Vα 2 | 5 | HAP 26 | 5'-GTGTTCCCAGAGGGAGCCATTGCC-3' | 2.1, 2.2 |
| Vα 3 | 6 | HAP 05 | 5'-GGTGAACAGTCAACAGGGAGA-3' | 3.1 |
| Vα 4 | 7 | HAP 08 | 5'-ACAAGCATTACTGTACTCCTA-3' | 4.1 |
| Vα 5 | 8 | HAP 35 | 5'-GGCCCTGAACATTCAGGA-3' | 5.1 |
| Vα 6 | 9 | HAP 01 | 5'-GTCACTTTCTAGCCTGCTGA-3' | 6.1 |
| Vα 7 | 10 | HAP 21 | 5'-AGGAGCCATTGTCCAGATAAA-3' | 7.1, 1.2 |
| Vα 8 | 11 | HAP 41 | 5'-GGAGAGAATGTGGAGCAGCATC-3' | 8.1, 1.2 |
| Vα 9 | 12 | HAP 36 | 5'-ATCTCAGTGCTTGTGATAATA-3' | 9.1 |
| Vα 10 | 13 | HAP 58 | 5'-ACCCAGCTGGTGGAGCAGAGCCCT-3' | 10.1 |
| Vα 11 | 14 | HAP 02 | 5'-AGAAAGCAAGGACCAAGTGTT-3' | 11.1 |
| Vα 12 (Ab13) | 15 | PGA 5 | 5'-CAGAAGGTAACTCAAGCGCAGACT-3' | 12.1 |
| Vα 13 | 16 | AB 11 | 5'-GCTTATGAGAACACTGCGT-3' | 13.1 |
| Vα 14 | 17 | AB 21 | 5'-GCAGCTTCCCTTCCAGCAAT-3' | 14.1 |
| Vα 15 | 18 | AC 24 | 5'-AGAACCTGACTGCCCAGGAA-3' | 15.1 |
| Vα 16 | 19 | AE 212 | 5'-CATCTCCATCGGACTCATATGA-3' | 16.1 |
| Vα 17 | 20 | AF 211 | 5'-GACTATACTAACAGCATGT-3' | 17.1 |
| Vα 18 | 21 | AC 9 | 5'-TGTCAGGCAATGACAAGG-3' | 18.1 |
| Cα (Ab51) | 22 | PGA 5 | 5'-AATAGGTCGACACACTTGTCACTGGA-3' | Cα |

TABLE 2

T-Cell Receptor a Expression in Brain Plaques Of Multiple Sclerosis Patients.

| | Vα 1 | Vα 2 | Vα 3 | Vα 4 | Vα 5 | Vα 6 | Vα 7 | Vα 8 | Vα 9 | Vα 10 | Vα 11 |
|---|---|---|---|---|---|---|---|---|---|---|---|
| Experiment No. 1 | | | | | | | | | | | |
| MS Br1 | 383 | 4650 | 760 | 520 | 240 | 850 | 826 | 1566 | 450 | 45860 | 5430 |
| MS Br2 | 140 | 824 | 523 | 310 | 830 | 415 | 660 | 23200 | 1750 | 29630 | 623 |
| MS Br3 | 638 | 313 | 276 | 410 | 817 | 1520 | 210 | 15860 | 16310 | 21200 | 838 |
| C Br4 | 235 | 1100 | 135 | 115 | 286 | 7300 | 427 | 960 | 1036 | 317 | 560 |
| C Br5 | 580 | 875 | 180 | 490 | 110 | 846 | 160 | 324 | 780 | 120 | 344 |
| C Br6 | 137 | 290 | 133 | 530 | 836 | 640 | 910 | 110 | 140 | 350 | 670 |
| Experiment No. 2 | | | | | | | | | | | |
| MS Br1 | 1650 | 3956 | 1450 | 790 | 547 | 545 | 1170 | 343 | 1856 | 32870 | 513 |
| MS Br2 | 967 | 340 | 1419 | 1575 | 3866 | 2837 | 1848 | 13373 | 2974 | 17337 | 1550 |
| MS Br3 | 666 | 726 | 1198 | 790 | 1769 | 258 | 576 | 35270 | 18990 | 19138 | 948 |
| C Br4 | 1507 | 660 | 1740 | 1790 | 553 | 706 | 4540 | 4410 | 1333 | 584 | 919 |
| C Br5 | 896 | 1670 | 2370 | 5000 | 2826 | 418 | 862 | 8175 | 2048 | 1307 | 1734 |
| C Br6 | 883 | 1727 | 716 | 865 | 610 | 1334 | 9514 | 1033 | 1256 | 1130 | 636 |
| PBL (PHA) | 9434 | 19464 | 8288 | 18434 | 18820 | 10483 | 12800 | 14886 | 13980 | 23040 | 11448 |

| | Vα 12 | Vα 13 | Vα 14 | Vα 15 | Vα 16 | Vα 17 | Vα 18 | Vβ 8 | Actin |
|---|---|---|---|---|---|---|---|---|---|
| Experiment No. 1 | | | | | | | | | |
| MS Br1 | 36380 | 3618 | 367 | 280 | 289 | 226 | 442 | 170 | 104450 |
| MS Br2 | 49125 | 456 | 220 | 317 | 12460 | 3572 | 338 | 280 | 79120 |
| MS Br3 | 2050 | 302 | 225 | 462 | 3633 | 482 | 470 | 630 | 58358 |
| C Br4 | 726 | 485 | 278 | 466 | 630 | 545 | 830 | 900 | 65996 |
| C Br5 | 138 | 762 | 755 | 876 | 860 | 715 | 570 | 860 | 66393 |
| C Br6 | 1030 | 1095 | 2000 | 437 | 775 | 240 | 330 | 710 | 139337 |
| Experiment No. 2 | | | | | | | | | |

TABLE 2-continued

T-Cell Receptor a Expression in Brain Plaques Of Multiple Sclerosis Patients.

| MS Br1 | 12978 | 866 | 868 | 3190 | 280 | 1048 | 1127 | 440 | 38593 |
|---|---|---|---|---|---|---|---|---|---|
| MS Br2 | 33020 | 1487 | 1072 | 3148 | 17968 | 1446 | 980 | 1338 | 32460 |
| MS Br3 | 2690 | 587 | 880 | 815 | 945 | 946 | 1570 | 630 | 22415 |
| C Br4 | 765 | 860 | 206 | 590 | 713 | 2748 | 526 | 864 | 31285 |
| C Br5 | 836 | 737 | 1040 | 2097 | 2925 | 1025 | 5276 | 4478 | 33018 |
| C Br6 | 170 | 4636 | 1300 | 1930 | 1167 | 764 | 5915 | 370 | 29451 |
| PBL (PHA) | 16968 | 16536 | 17750 | 30512 | 16544 | 21132 | 19732 | ND | ND |

The T-cell receptors present in the brain of MS patient 1 were amplified and subjected to gel electrophoresis, where control brain cDNA, MS parietal region brain cDNA, MS occipital region brain cDNA, PGA5, a full length TcR α cDNA (Sim, et al., Nature 312,771–775 (1984)) were compared. Two μl of cDNA was combined in a 100 μl reaction volume, with 1 unit of DNA Taq polymerase (Perkin Elmer-Cetus), 10 μl 10× reaction buffer, 50 μM each dNTPs, and 1 μM of each primer. The PCR profile used was: denaturation 96° C. for 60 sec., annealing 45° C. for 60 sec. and extension 72° C. for 120 sec., for a total of 35 cycles on a DNA Thermal Cycler (Perkin Elmer-Cetus). One tenth of each sample was independently run in a 4% Nusiev gel, and an appropriate size fraction was cut from the gel. The agarose piece was frozen and thawed 3 times, and 2 μl of the supernatant were directly reamplified with the same primers for an additional 25 cycles. Actin sequences were successfully amplified from brain cDNA, but not from the PGA 5 control using the following primers (SEQ ID NO:23) and (SEQ ID NO: (5'-ACGAAGACGGACCACCGCCCTG-3', 5'-CACGTTGTGGGTGACGCCGTC-3'). Vα and Cα transcripts were amplified from both MS brain cDNA and PGA 5 templates, but not from the control MS brain cDNA with primers AB 13–14 (SEQ ID NO:25) and (SEQ ID NO:26) (5'-CAGAAGGTAACTGCAGCGCAGACT-3', 5'-TTGGGGATCCAGAGCACAGAAGTATACTGC-3'), which include the restriction sites PstI and BamHI and define a 286 bp fragment of the Vα12.1 region gene and AB 41–42 SEQ ID NO:27) and (SEQ ID NO: (5'-CAGAACCCTGACCCTGCCGTGTAC-3', 5'-GTGTCCACAGTTTAGGTTCGTATCTGT-3', which include a SalI site and define a bp fragment of the Cα region transcript) respectively. Note that rearranged TcRα sequences could be amplified from cDNA of the MS brain prepared from the occipital region using the Vα12.1 primer AB 13 and Cα primer AB 42.

Junctional region sequences were derived from the Vα12.1-JC amplification from the occipital region of the MS brain. 100 μl of the PCR reaction were phenol:chloroform extracted twice with 1/1 volume, chloroform extracted once with 1/1 volume, and dialyzed through a Centricon 30 (Amicon) with 2 ml of TE buffer for 30 min. at 5000 rpm. The sample was recovered and the DNA digested for 3 hr. with BamHI and PstI (or SalI). After digestion, the sample was phenol:chloroform extracted and then chloroform extracted once, passed through the same Centricon column as described above, and brought to a final volume of 20 μl. 3 μl of sample was put into a 10 μl ligation with 200 ng of Bam HI/PstI or BamHI/SalI cut M13mpl8 and ligated overnight at 16° C. with T4 DNA ligase (New England Biolabs). Transformation into E. coli JM101 was done according to standard procedures and positive plaques were selected by hybridization to $^{32}$P-labelled TcR probes. 30 clones were sequenced by the dideoxy chain termination method using $^{35}$S-dATP and Sequenase (U.S. Biochemicals).

The above results showed in the amplification of the cDNA of one patient and the actin control, that actin could be amplified from the brain cDNAs but not from PGA5, a full length cDNA clone which contains the Vα12.1 segment. Also evident were lesser amounts of a smaller PCR product corresponding to the Va12.1 gene in the patient but not in the control sample. To ensure that the one Vα family was amplified, genomic and brain Vα12.1 PCR products were analyzed using restriction endonucleases and compared to the known restriction map. Only the expected fragments were observed, consistent with the notion that only the Vα12.1 family was amplified. When colonies containing cloned Vα PCR products were screened with a Vα12.1 region probe, approximately 20% were positive. DNA from several of these colonies was sequenced and found to be identical to the published Vα12.1 sequences (Sim, et al., Nature 312, 771–775 (1984)). Thus, the restriction fragment length polymorphisms (RFLP) recently associated with MS susceptibility must be in a sequence flanking to the TcR Vα gene. (Oksenberg, et al., Proc. Natl. Acad. Sci. USA 86, 988–992 (1989)).

The above results demonstrated that PCR could amplify the receptor transcripts from post-mortem brain samples, starting from 5 μg of total RNA without the necessity of in vitro expansion of T-cells. Similarly, Cα sequences were amplified from MS brain cDNAs, but not from the control sample. A subsequent amplification using primers complementary to the Vα and the Cα TcR regions produced a major band when the control PGA5 and cDNA from the occipital region of the MS brain were used as a template, indicating the presence of rearranged TcR transcripts in the sample. The Vα and Cα amplifications from the parietal region brain library most probably represent real transcripts from rearranged chromosomes, as has been found in other cDNA libraries from T-cell lines (Loh, et al., Science 243, 217–220 (1989).

No PCR product was observed using primers corresponding to the Vβ8 family, even though these primers are able to amplify the gene from buffy coat extracted genomic DNA. This TcR V region was recently reported to be associated with susceptibility to MS (Beall, et al., J. Neuroimmunol 21, 59–66 (1989).

To provide further evidence that the DNA produced during the PCR amplification was an authentic amplified product of rearranged TcR genes, the PCR products were sequenced after double screening of colonies with Vα and Cα probes. Only two different J regions were seen in the thirty sequences examined, both different from the PGA5 Jα sequence. Eleven sequences contain the Jα O family found in clone HAP41 (Yoshikai, et al., J. Exp. Med. 164, 90–103 (1986). Fourteen sequences had a previously undescribed Jα sequence (SEQ ID NO:1), GGGTACCGAGATGACGAAC-CCACCTTTGGGACAGGCACT-CAGCTAAAAGTGGAACTC.

In order to completely analyze the TcR Vα usage in MS brains, 18 different Vα specific oligonucleotides for use as 5' PCR primers, based on published sequences for these gene families were prepared (Yoshikai, et al., supra (1986); Kline, et al., Proc. Natl. Acad. Sci. USA 84, 6884–6888 (1987)). Optimal conditions for amplification with each primer were ascertained with genomic DNA using a specific 3' Vα primer for each TcR Vα family and with reverse-transcribed RNA isolated from PHA stimulated peripheral blood lymphocytes. Using 5' Vα primers and a common 3' Cα primer, the results from amplification of brain cDNA show that in each brain only a few TcR V gene families are preferentially expressed and rearranged. The Vα 10 and 12 were detected in MS brains 1 and 2. MS brain 2 also expressed the Vα 8 and the Vα 16. In MS brain 3, the Vα 8, 9 and 10 families were efficiently amplified. The Vα 10 was thus common to all three samples.

In order to analyze the usage of Vα genes, we analyzed cDNA reverse transcribed from mRNA isolated from uveal melanoma specimens. Eighteen different Vα specific oligonucleotides representing the major human TCR Vα families were used for the 5' primers and a Cα sequence was used for the 3'-primer (Table 1). Total RNA was extracted from each of eight uveal melanoma samples and was reverse transcribed. Total RNA from melanoma tissue was prepared in the presence of guanidinium thiocyanate in the method using RNAzol™ (Cinna/Biotec, Texas) (Choi, et al., Proc. Natl. Acad. Sci. USA 86, 8941 (1989)), and references cited therein). 2 µg of total RNA was used for the synthesis of single strand cDNA using reverse transcriptase. In a final volume of 20 µl 1×PCR buffer (50 mM KCl, 20 mM Tris-Cl, pH 8.4, 2.5 mM MgCl), 1 mM of NTP's, 20 units of RNAsin, 100 pmoles of random hexamer (Pharmacia) and 200 units of BRL MoMuLV reverse transcriptase were incubated with RNA (2 µg) for 40 minutes at 42° C. (Kamasaki, et al., Ibid., 85, 5698 (1988)). The reaction mixture was heated at 95° C. for 5 minutes, then quickly chilled on ice. The DNA was then ready for PCR. The resulting cDNA was amplified using individual sets of Vα-Cα primers with primers for melanotransferrin, a specific marker for melanoma. Each Vα primer yielded a band of 300 to 400 bp on ethidium bromide-staining of the electrophoresed PCR product.

Analysis of Vα expression in TIL from melanoma specimens is shown in Table 3.

TABLE 3

Usage of TCR Vα Gene in Uveal Melanomas

| Case Number | Vα Families | | | | | |
|---|---|---|---|---|---|---|
| 1 | Vα2 | | Vα7 | | | |
| 2 | | Vα6 | Vα7 | | | Vα13 |
| 3 | | | Vα7 | | | Vα13 Vα14 |
| 4 | | | Vα7 | | | Vα13 Vα14 |
| 5 | | | Vα7 | | | |
| 6 | | | Vα7 | Vα10 | | |
| 7 | | | | | Vα12 | |
| 8 | | | Vα7 Vα8 Vα9 | | | Vα14 |

TCR Vα families expressed in human uveal melanoma. A single stranded cDNA sample was amplified using Vα-specific primer with a Cα primer at a final concentration of 1 µM in each reaction. The amplification was performed with 2.5 units of Taq polymerase (ampli Taq™; Perkin Elmer) on a Perkin-Elmer DNA thermal cycler (Cetus). The PCR cycle profile was 95° C. denaturation for 1 min. annealing of primers at 55° C. for 1 min, extension primers at 72° C. for 1 min for 35 cycles. PCR products were separated on 1% regular agarose/3% Nusive™ agarose gels (FMC Corporation) and expression of Vα families was considered positive when a rearranged band (300–400 bp) was visualized with ethidium-bromide staining. Experiments were repeated three times per sample. Results were identical with a different aliquot of each sample.

All TCR 5' primers amplify TCR sequences from germline DNA using a specific 3' Vα primer for each family. We have detected a Vα-Cα rearrangement of all TCR gene members in a variety of activated T-cells including single rearrangements of specific Vα members in T-cell clones reactive to pertussis toxin, to Borrelia bergdorfei, and alloantigens as well as rearrangements of all Vα members in pooled T-cells stimulated by PHA.

Among seven of eight cases only one to three Vα genes (Vα 7, 8, 9, 12 and 14) were detected. In seven of eight cases Vα7 was expressed and rearranged. Melanotransferrin was amplified in all cases. Amplification artifacts due to contaminating DNA were excluded by performing controls in which no amplification was observed without cDNA samples or with genomic DNA. Identical results were obtained after a further experiment using different aliquots of each patient's tumor.

The amplified products obtained with the Vα7 primer were further identified by hybridization with Vα7 and Cα specific oligonucleotide probes. In all cases where the Vα7 rearranged product was visualized on agarose gel electrophoresis with ethidium bromide staining, a positive hybridization was observed on dot blotting to the Vα7 oligonucleotide probe (SEQ ID NO:29) (5'-CTG GAG CTC CTG TAG AAG GAG-3'). Amplified melanotransferrin did not hybridize with this probe at all. In addition, the Vα7-Cα amplified product hybridized to a Cα oligonucleotide probe (SEQ ID NO:30) (5'-CAG AAC CCT GAC CCT GCC GTG TAC-3') but not with Vα1 and Vα4 specific oligonucleotide probes.

Additional characterization of the Vα7 amplified products was obtained by restriction mapping with the endonucleases, DdeI, KpnI and HinfI. The restriction pattern was consistent with the known map of Vα7. (Yoskikai, et al., J. Exp. Med., 114, 90 (1968)).

In this manner, the variable region(s) associated with each of the different neoproliferative tissues may be determined. A substantially homogeneous composition of T-cells may then be administered for treatment of the particular neoproliferative tissue. Instead of isolating mature T-cells, pre-T-cells may be isolated, activated with the tumor tissue or appropriate protein and the T-cells having the appropriate variable region(s) isolated and used for therapy. The T-cells may also be used for prophylaxis by administering T-cell compositions after chemotherapy, irradiation and/or surgical intervention.

TCR Vα and Vβ rearrangements were studied in 16 MS brains and in 10 control brains. TCRVα-Jα-Cα and Vβ-Dβ-Jβ-Cβ rearrangements were confirmed with Southern blotting and hybridization of the PCR product obtained with amplification with 1 of 18 Vα or 1 of 21 Vβ specific oligonucleotide primers. The following table indicates the primers.

TABLE 4

T-Cell Receptor α and β Primers.

| Seq ID No. | Primer | Sequence | Seq ID No. | Primer | Sequence |
|---|---|---|---|---|---|
| 4 | Vα 1 | 5'-TTGCCCTGAGAGATGCCCAGAG-3' | 31 | Vβ 1 | 5'-GCACAACAGTTCCCTGACTTGCAC-3' |
| 5 | Vα 2 | 5'-GTGTTCCAGAGGGAGCCATTGCC-3' | 32 | Vβ 2 | 5'-TCATCAACCATGCAAGCCTGACCT-3' |
| 6 | Vα 3 | 5'-GGTAGAACAGTCAACAGGGAGA-3' | 33 | Vβ 3 | 5'-GTCTCTAGAGAGAAGAAGGAGCGC-3' |
| 7 | Vα 4 | 5'-ACAAGCATTACTGTACTCCTA-3' | 34 | Vβ 4 | 5'-ACGATCCAGTGTCAAGTCGT-3' |
| 8 | Vα 5 | 5'-GGCCCTGAACATTCAGGA-3' | 35 | Vβ 5.1 | 5'-ATACTTCAGTGAGACACAGAGA-3' |
| 9 | Vα 6 | 5'-GTCACTTTCTAGCCTGCTGA-3' | 36 | Vβ 5.2 | 5'-TTCCCTAACTATAGCTCTGGCTG-3' |
| 10 | Vα 7 | 5'-AGGAGCCATTGTCCAGATAAA-3' | 37 | Vβ 6 | 5'-AGGCCTGAGGGATCCGTCTC-3' |
| 11 | Vα 8 | 5'-GGAGAGAATGTGGAGCAGCATC-3' | 38 | Vβ 7 | 5'-AGGCCTGAGGGATCCGTCTC-3' |
| 12 | Vα 9 | 5'-ATCTCAGTGCTTGTGATAATA-3' | 39 | Vβ 8 | 5'-CCTGAATGCCCCAACAGCTCTC-3' |
| 13 | Vα 10 | 5'-ACCCAGCTGCTGGAGCAGAGCCCT-3' | 40 | Vβ 9 | 5'-CTAAATCTCCAGACAAAGCTCAC-3' |
| 14 | Vα 11 | 5'-AGAAAGCAAGGACCAAGTGTT-3' | 41 | Vβ 10 | 5'-TCCAAAAACTCATCCTGTACCT-3' |
| 15 | Vα 12 | 5'-CAGAAGGTAACTCAAGCGCAGACT-3' | 42 | Vβ 11 | 5'-TGTTCTCAAACCATGGGCCATGAC-3' |
| 16 | Vα 13 | 5'-GCTTATGAGAACACTGCGT-3' | 43 | Vβ 12 | 5'-GATACTGACAAAGGAGAAGTCTCAGAT-3' |
| 17 | Vα 14 | 5'-GCAGCTTCCCTTCCAGCAAT-3' | 44 | Vβ 13 | 5'-GGTGAGGGTACAACTGCC-3' |
| 18 | Vα 15 | 5'-AGAACCTGACTGCCCAGGAA-3' | 45 | Vβ 14 | 5'-ACCCAAGATACCTCATCACAG-3' |
| 19 | Vα 16 | 5'-CATCTCCATGGACTCATATGA-3' | 46 | Vβ 15 | 5'-AGTGTCTCTCGACASGGCACAG-3' |
| 20 | Vα 17 | 5'-GACTATACTAACAGCATGT-3' | 47 | Vβ 16 | 5'-CATGATAATCTTTATCGACGTGTT-3' |
| 21 | Vα 18 | 5'-TGTCAGGCAATGACAAGG-3' | 48 | Vβ 17 | 5'-AGCCCAATGAAAGGAACACAGTCAT-3' |
| | | | 49 | Vβ 18 | 5'-AGCCCAATGAAAGGACACAGTCAT-3' |
| | | | 50 | Vβ 19 | 5'-ACCCCCGAAAAAGGACATACT-3' |
| | | | 51 | Vβ 20 | 5'-CTCTGAGGTGCCCCAGAA-3' |
| 22 | Cα | 5'-AATAGGTCGACAGACTTGTCACTGGA-3' | 52 | Cβ | 5'-TTCTGATGGCTCAAACAG-3' |

Coded human brain samples were obtained from the Rocky Mountain Multiple Sclerosis Center in Englewood, Colo. and La Trobe University, Victoria, Australia. Samples included rapidly frozen and cryopreserved autopsy samples from different regions of 16 MS brains and 10 non-MS controls. Each sample was homogenized and the total RNA was extracted using the RNAzol method (Cinna/Biotecx, Friendswood, Tex.), (Chonzynski and Sacchi, Anal. Biochem. 162, 156 (1987)). Approximately 0.25 μg of total RNA was reverse transcribed into a first cDNA strand in a 10 μl reaction containing 1 μl 10×PCR buffer (100 mM Tris-HCl pH 8.3, 500 mM KCl 15 mM $MgCl_2$, 0.01% (w/v) gelatin (Perkin, Elmer, Norwalk, Conn.), 1 μl of 10 mM dioxynucleotide triphosphates, 0.25 U random hexamers (Pharmacia, Piscataway, N.J.) and 100 U of Superscript MuLV-reverse transcriptase (BRL, Gaithersburg, Md.). The reaction mix was incubated at room temperature for 10 min, followed by incubations at 42° C. for 45 minutes and 95° C. for 5 minutes. The mix was then quick chilled on ice. cDNA was subjected to enzymatic amplification by the PCR method. 10 μl cDNA was combined in a 50 μl reaction mix with 4 μl 10×PCR buffer, 1.25 U Taq polymerase, 0.5 μM of Cα or Cβ primer and 0.5 μM of Vα or Vβ specific oligonucleotide primer (Table 4).

The PCR profile used was: Denaturation 95° C. for 60 sec annealing 55° C. for 60 sec and extension 72° C. for 60 sec for 35 cycles in a DNA Thermal Cycler.

DNA Isolation and HLA Typing: High molecular weight DNA was extracted from tissue samples according to standard procedures. HLA-DRB1, DQA1, DQB1 and DPB1 typing was performed by PCR, dot blotting and hybridization with allele specific oligonucleotide probes (Helmuth, et al., Am. J. Hum. Genet. 47, 515 (1990); and Bugawan, et al., Immunogenetics 32, 231 (1990)).

Specificity was confirmed by identifying single rearrangements in antigen specific T-cell clones for B. bergdorfei, pertussis toxin and acetylcholine receptor. No amplification was detected in a colon carcinoma cell line. All samples were coded with the molecular biologist blinded to the origin of the specimen other than 3 MS brains and 3 controls.

A limited number of TCR Vα gene arrangments were seen in 15 of 16 of the MS specimens. The Vα families which are most frequently observed undergoing rearrangement are 8–10, 12 and 16, while less frequently rearrangements are observed with Vα1, 5 and 7. Table 5 is divided into four parts. Column 1 indicates the different samples from different patients; the second to sixth columns refer to the HLA-Class II profile of the individual patients. Column 7 indicates whether one or more plaques were involved, designating the individual plaques by letters. The remaining columns refer to the rearranged Vα subunit, where the presence of a number indicates that that Vα subunit was rearranged.

TABLE 5

TCR Vα

| Sample | DRB1 | DQA1 | DQB1 | DPB1 | DR(Dw) | Plaque | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|---|---|---|---|---|
| MS | | | | | | | | | | | | | | | | | | | | | | | | |
| KL(C) | 0601,1501 | 0102,0401/0601 | 04,0602 | 0401,0401 | 2(w2),w6 | a | | 2 | | | | | | | | | | 12 | 13 | | | | | |
| | | | | | | b | | | | | | | | 8 | | 10 | | | | | | 16 | | |
| LJ(C) | 1101,1501 | 0102,0501 | 0301,0602 | 0401,0402 | 2(w2),w11 | c | 1 | | | | | | | | | | | | | | | 16 | | |
| | | | | | | a | 1 | | | | 5 | | | | | | | | | 14 | | 16 | | |
| | | | | | | b | | | | | 5 | | | | | | | | 13 | 14 | | 16 | | |
| | | | | | | c | | | | | | | | | | 10 | | | 13 | 14 | | 16 | | |
| MK(C) | 1501,1501 | 0102,0102 | 0602,0603 | 0401,1401 | 2(w2),2(w) | d | | | | | 5 | | 7 | | | | | | 13 | 14 | | 16 | | |
| ZD(C) | 1101,1501 | 0102,0501 | 0301,0602 | 0401,0402 | 2(w2),211 | e | | | | | | | | | | | | | 13 | 14 | | | | |
| TJ(C) | 1501,1601 | 0102,0102 | 0502,0602 | 0401,0401 | 2(w2),2(w21) | a | 1 | 2 | | | 5 | | | 8 | | | | 12 | 13 | 14 | | 16 | 17 | |
| MS2(A) | 0101/2,1501 | 0101,0102 | 0501,0602 | 0402,0501 | 1,2(w2) | a | 1 | | | | | | | | | | | | | | 15 | | | |
| GL(A) | 07,1501 | 0102,0201 | 0201,0802 | 0401,1101 | 2(W2),7 | a | | | | | | | 7 | | | | | 12 | 13 | | | 16 | | |
| | | | | | | b | | | | | | | | | | | | 12 | 13 | | | 16 | | |
| PM10(A) | 07,1501 | 0102,0201 | 0201,0602 | 0401,0901/1701 | 2(w2),7 | c | | | | 4 | 5 | | 7 | | | | | | | 14 | | 16 | 17 | |
| | | | | | | a | | | | | 5 | | 7 | 8 | | | | 12 | | 14 | | | 17 | |
| TF(C) | 0404,1601 | 0102,0301 | 0302,0602 | 0201,1101 | 2(w-),4(w14) | b | | | | | | | 7 | | 9 | | | 12 | 13 | 14 | | 16 | 17 | |
| | | | | | | a | | | | | | | | | | | | 12 | | | | | 17 | |

TCR Vβ

| Sample | DRB1 | DQA1 | DQB1 | DPB1 | DR(Dw) | Plaque | 1 | 2 | 3 | 4 | 5.1 | 5.2 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|---|---|---|---|---|
| MS | | | | | | | | | | | | | | | | | | | | | | | | | | | |
| KL(C) | 0601,1501 | 0102,0401/0601 | 04,0602 | 0401,0401 | 2(w2),w6 | a | | | | | | 5.2 | 6 | | | | | | 12 | | | | | | | | |
| | | | | | | b | | | | | | 5.2 | 6 | | | | | | | | 14 | | | | | | |
| | | | | | | c | | 2 | | | | 5.2 | | | 8 | | | | | | | | 17 | 18 | | | |
| LJ(C) | 1101,1501 | 0102,0501 | 0301,0602 | 0401,0402 | 2(w2),w11 | a | 1 | 2 | | | 5.1 | 5.2 | | | | | | | 12 | | | | 17 | 18 | | | |
| | | | | | | b | | | | | 5.1 | 5.2 | | | | | | | 12 | | | | | 18 | | | |
| MK(C) | 1501,1501 | 0102,0102 | 0602,0603 | 0401,1401 | 2(w2),2(w) | c | | | 3 | | 5.1 | 5.2 | 6 | 7 | | | | 11 | 12 | | | | | | | | |
| | | | | | | d | | 2 | 3 | | 5.1 | 5.2 | 6 | 7 | | | | 11 | | | | | 17 | 18 | | | |
| | | | | | | e | | 2 | 3 | | | 5.2 | 6 | 7 | | | | | 12 | | | | 17 | | | | |
| ZD(C) | 1101,1501 | 0102,0501 | 0301,0602 | 0401,0402 | 2(w2),211 | a | | | 3 | | 5.1 | 5.2 | 6 | 7 | | 9 | | 11 | | | | | | | | | |
| TJ(C) | 1501,1601 | 0102,0102 | 0502,0602 | 0401,0401 | 2(w2),2(w21) | a | 1 | 2 | | 4 | | 5.2 | 6 | 7 | 8 | 9 | | | | | | | | | | | |
| MS2(A) | 0101/2,1501 | 0101,0102 | 0501,0602 | 0402,0501 | 1,2(w2) | a | | | | | 5.1 | 5.2 | 6 | 7 | 8 | 9 | | | | | | | | | | | |
| GL(A) | 07,1501 | 0102,0201 | 0201,0802 | 0401,1101 | 2(W2),7 | a | | | 3 | | | 5.2 | 6 | | 8 | 9 | | | 12 | 13 | 14 | 15 | | 18 | | | |
| | | | | | | b | | | 3 | | | 5.2 | 6 | | 8 | 9 | | | 12 | 13 | | | | 18 | | | |
| | | | | | | c | | | | | | | 6 | | | | | | | | | | | | | | |
| PM10(A) | 07,1501 | 0102,0201 | 0201,0602 | 0401,0901/1701 | 2(w2),7 | a | | | | | | 5.2 | 6 | 7 | 8 | 9 | 10 | | | | | | | | | | |
| TF(C) | 0404,1601 | 0102,0301 | 0302,0602 | 0201,1101 | 2(w-),4(w14) | b | | | | 4 | | 5.2 | | | 8 | 9 | 10 | | | | 14 | 15 | | | | | |
| | | | | | | a | | | | | | | 6 | 7 | 8 | | | | | | 15 | | | 17 | | | |

TABLE 5-continued

| Sample | HLA-CLASS II | | | | | Plaque | TCR Vα | | | | | | | | | | | | | | | | |
|---|---|---|---|---|---|---|---|---|---|---|---|---|---|---|---|---|---|---|---|---|---|---|---|
| | DRB1 | DQA1 | DQB1 | DPB1 | DR(Dw) | | 1 | 2 | 3 | 4 | 5 | 6 | 7 | 8 | 9 | 10 | 11 | 12 | 13 | 14 | 15 | 16 | 17 | 18 |
| ZI(C) | 0301,0801 | 04/06, 04/05/06 | 0201,04 | 0401,0601/ 1601 | 3,w6 | a | 1 | | | | 5 | | | | | | | | | | | 16 | 17 | |
| RH(C) | 0101/02, 1001 | 0101,0101 | 0501,0601 | 0201,0402 | 1,210 | a | 1 | | | | 5 | | | 8 | 9 | | | 12 | | | | | | |
| MS1(A) | 0301,1303 | 0401,0401 | 0201,0301 | 0101,0201 | 3,w13 | a | | | | | | | | 8 | | 10 | | 12 | | | | | | |
| MS4(A) | 0301,1302 | 0102,0501 | 0201,0604 | 0201,0201 | 3,w13 | a | | | | | | 6 | | | | 10 | | 12 | | | | | | |
| HY(A) | 1303,1401 | 0101,0501 | 0301,0603 | 0201,0402 | w13,w14 | a | | | | | | | | | | | 11 | 12 | | | | 16 | | |
| | | | | | | b | | | | | | | | | | | 11 | 12 | | | | 16 | | |
| KI(A) | 0404,1301 | 0103,0301 | 0302,0803 | 0402,0601 | 4(w14),w13 | c | | | | | 5 | 6 | | | | | | | | | | | | |
| MS5(A) | 0101/ 1401 | 0101,0101 | 0501,0603 | 0301,0401 | 1,w14 | a | | | | | 5 | 6 | | | | | | | | | | 16 | | |
| CONTROLS | | | | | | | | | | | | | | | | | | | | | | | | |
| PM1125(A) | 0402,1401 | 0101,0301 | 0302,0603 | 0401,0401 | 4(w10),w14 | | | | | | | | | | | | | | | | | | | |
| PM602(A) | 0301,1302 | 0102,0501 | 0201,0804 | 0401,0601 | 3,w13 | | | | | | | | | | | | | | | | | | | |
| PM1367(A) | ND | | | | | | | | | | | | | | | | | | | | | | | |
| C1(A) | ND | | | | | | | | | | | | | | | | | | | | | | | |
| C2(A) | ND | | | | | | | | | | | | | | | | | | | | | | | |

| Sample | HLA-CLASS II | | | | | Plaque | TCR Vβ | | | | | | | | | | | | | | | | | | | |
|---|---|---|---|---|---|---|---|---|---|---|---|---|---|---|---|---|---|---|---|---|---|---|---|---|---|---|
| | DRB1 | DQA1 | DQB1 | DPB1 | DR(Dw) | | 1 | 2 | 3 | 4 | 5.1 | 5.2 | 6 | 7 | 8 | 9 | 10 | 11 | 12 | 13 | 14 | 15 | 16 | 17 | 18 | 19 | 20 |
| ZI(C) | 0301,0801 | 04/06, 04/05/06 | 0201,04 | 0401,0601/ 1601 | 3,w6 | a | 1 | 2 | | 4 | | | | | 8 | 9 | 10 | | 12 | | | | | 17 | | | |
| RH(C) | 0101/02, 1001 | 0101,0101 | 0501,0601 | 0201,0402 | 1,210 | a | | | | | | | | 7 | | | | | | | | | | | | | |
| MS1(A) | 0301,1303 | 0401,0401 | 0201,0301 | 0101,0201 | 3,w13 | a | | | 3 | 4 | | | | | 8 | | | | 12 | | | | | | | | |
| MS4(A) | 0301,1302 | 0102,0501 | 0201,0604 | 0201,0201 | 3,w13 | a | | | 3 | 4 | 5.1 | | | 7 | 8 | | | | 12 | | | | | | | | |
| HY(A) | 1303,1401 | 0101,0501 | 0301,0603 | 0201,0402 | w13,w14 | a | | | 3 | 4 | | ND | | | 8 | 9 | | | 12 | | | | | | 18 | | |
| | | | | | | b | | | | | | | | | 8 | | | | | | | | | | 18 | | |
| KI(A) | 0404,1301 | 0103,0301 | 0302,0803 | 0402,0601 | 4(w14),w13 | c | | | | | | | 6 | | | | | | | | 14 | | | | | | |
| MS5(A) | 0101/ 1401 | 0101,0101 | 0501,0603 | 0301,0401 | 1,w14 | a | | | | 4 | | | | | | | | | | | | | | | | | |
| CONTROLS | | | | | | | | | | | | | | | | | | | | | | | | | | | |
| PM1125(A) | 0402,1401 | 0101,0301 | 0302,0603 | 0401,0401 | 4(w10),w14 | | | | | | | | | | | | | | | | | | | | | | |
| PM602(A) | 0301,1302 | 0102,0501 | 0201,0804 | 0401,0601 | 3,w13 | | | | | | | | | | | | | | | | | | | | | | |
| PM1367(A) | ND | | | | | | | | | | | | | | | | | | | | | | | | | | |
| C1(A) | ND | | | | | | | | | | | | | | | | | | | | | | | | | | |
| C2(A) | ND | | | | | | | | | | | | | | | | | | | | | | | | | | |

TABLE 5-continued

| Sample | HLA-CLASS II DRB1 | DQA1 | DQB1 | DPB1 | DR(Dw) | Plaque | TCR Vα 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|---|---|---|---|---|
| C3(A) | ND | | | | | | | | | | | | | | | | | | | | | | | |
| LV(C) | 0404,0405 | 0301,0301 | 0302,04 | 0301,0401 | 4(w14),4(w15) | | | | | | | | | | | | | | | | | | | |
| ME(C) | 0406,1301 | 0103,0301 | 0301,0603 | 0201,0401 | 4,w13 | | | | | | | | | | | | | | | | | | | |
| OR(C) | 1402,1501 | 0102,0103 | 0502,0603 | 0301,0401 | 2(w-),w14 | | | | | | | | | | | | | | | | | | | |
| MO(C) | 0301,0401 | 0301,0501 | 0201,0301 | 0301,1101 | 3,4(w4) | | | | | | | | | | | | | | | | | | | |

| Sample | HLA-CLASS II DRB1 | DQA1 | DQB1 | DPB1 | DR(Dw) | Plaque | TCR Vβ 1 | 2 | 3 | 4 | 5.1 | 5.2 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|---|---|---|---|---|
| C3(A) | ND | | | | | | | | | | | | | | | | | | | | | | | | | | |
| LV(C) | 0404,0405 | 0301,0301 | 0302,04 | 0301,0401 | 4(w14),4(w15) | | | | | | | | | | | | | | | | | | | | | | |
| ME(C) | 0406,1301 | 0103,0301 | 0301,0603 | 0201,0401 | 4,w13 | | | | | | | | | | | | | | | | | | | | | | |
| OR(C) | 1402,1501 | 0102,0103 | 0502,0603 | 0301,0401 | 2(w-),w14 | | | | | | | | | | | | | | | | | | | | | | |
| MO(C) | 0301,0401 | 0301,0501 | 0201,0301 | 0301,1101 | 3,4(w4) | | | | | | | | | | | | | | | | | | | | | | |

As evidence by the results in Table 5, in one specimen, no Vα genes of the 18 families surveyed were rearranged, although this patient had two Vβ rearrangements. The number of TCR Vα genes transcribed ranged from 0 to 9 per brain, with a mean of 4.4±2.8 (±1 SD). TCR Vβ rearrangements were more diverse, with a range of 2 to 13 per brain, with a mean of 7.0±3.4 (±1 SD). TCR Vα or Vβ transcripts were not detected in any of the 10 brains of individuals who died of non-neurologic diseases.

All of the 16 MS patients were typed for the Class II HLA loci HLA-DRB1, DQA1, DQB1 and DPB1 using PCR and sequence-specific oligonucleotide probe hybridization. Eight of 16 patients were DRB1,*1501, DQA1*0102, DQB1*0602 and either DPB1*0401 or 0402. This molecular HLA-DR:DQ haplotype, which corresponds to the cellular type HLA-DR2Dw2, is associated with increased susceptibility to MS in certain caucasoid populations. Patients who were of the above indicated molecular phenotype showed an increased frequency of certain Vα and Vβ rearrangements.

TABLE 6

TCR Vβ Gene Usage Correlated with HLA-DR2 Molecular Phenotypes.

| TCR Vβ Rearrangement | Phenotype 1* | | | Phenotype 1a⁺ | | | Phenotype⁺ | | |
|---|---|---|---|---|---|---|---|---|---|
| | (+) MS | (−) MS | Control (−) | (+) MS | (−) MS | Control (−) | (+) MS | (−) MS | Control (−) |
| Vβ5.1 | 4/8 | 3/7 | 0/7 | 3/7 | 2/8 | 0/7 | 3/3$^{g,h}$ | 2/12$^g$ | 0/7$^h$ |
| Vβ5.2 | 7/8$^{a,b}$ | 2/7$^a$ | 0/7$^b$ | 7/7$^{c,d}$ | 2/8$^c$ | 0/7$^d$ | 2/3 | 7/12 | 0/7 |
| Vβ6 | 6/8 | 4/7 | 1/7 | 6/7$^{e,f}$ | 3/8$^e$ | 1/7$^f$ | 1/3 | 9/12 | 0/7 |

*Phenotype 1 = HLA-DR2Dw2/DRB1*1501/DQA1*0102
⁺Phenotype 1a = HLA-DR2DW2/DRB1*1501/DQA1*0102/DQB1*0602/DPB1*0401
⁺Phenotype 1b = HLA-DR2DW2/DRB1*1501/DQA1*0102/DQB1*0602/DPB1*0402
$^a X^2 = 5.4, P < .025$
$^b p = .002$ Fisher's Exact Test
$^c p = .011$ Fisher's Exact Test
$^d p = .0006$ Fisher's Exact Test
$^e X^2 = 3.6, p < .07$
$^f = .004$ Fisher's Exact Test
$^g p = .009$ Fisher's Exact Test
$^h p = .011$ Fisher's Exact Test As evidenced by the above Table 6, of 8 patients with the indicated phenotype, 7 had rearrangments of Vβ 5.2 and all 8 rearranged either Vβ 5.1 or 5.2 or both. Vβ 6 was transcribed in 6 of 8 MS brains with the above phenotype compared to 4 of 8 MS brains of patients who were not of the indicated phenotype and 6 control brains which were not of the indicated phenotype. Other frequent rearrangements seen in patients with the indicated phenotype were Vβ 7, 6/8, Vβ 12, 4/8, Vα 16, 6/8, Vα 5, Vα 7, Vα 12 and Vα 1 in 4/8.

Cloning and Sequencing of PCR-Amplified cDNA: PCR amplified cDNA samples were cloned into M13 for sequence analysis. Samples were digested with Pst I and SacI or with Pst I and Bam HI to cut restriction sites in the oligonucleotide primers. Centricon centrifugal microconcentrators (Amicon, Danvers Mass.) were used to concentrate and desalt the digested PCT products. After transformation in JM101 competent cells, clones containing TCR β inserts were identified by hybridization with a TCR β C-region HRP-labelled probe. Single stranded DNA from positive clones was prepared, and VDJCβ sequences determined by the dideoxy chain termination method with an AmpliTaq sequencing kit (Perkin-Elmer). The following Table 7 provides the results of the sequencing of Vβ5.2/3 for a number of different MSN patients. Beginning at the left, the first column indicates the sequence preceding the diversity sequence. The column headed N-D-N, indicates the diversity sequence, where a portion is genetically determined by the D exon, while other amino acids are introduced or removed, which is indicated by "N". J indicates the J exon and Cβ indicates the constant region sequence. The sequences form the CDR3 loop.

TABLE 7

CDR3 Sequences of TCR Rearrangements Amplified from NIS Brains and Controls

| Seq. ID | Vb5.2/3 | N-D-N | J | CB |
|---|---|---|---|---|
| | KL-1 | | | |
| 53 | LCASS | LPGTP | YGYFGSGTRLTVV (Jb 1.2) | EDLKN |
| 54 | LCASS | LPGTP | YGYTFGSGTRLTVV (Jb 1.2) | EDLKN |
| 55 | LCASS | LRLAN | SPLHFGNGTRLTVT (Jb 1.6) | EDLKN |
| 56 | LCASS | LDRL | YNSPLHFGNGTRLTVT (Jb 1.6) | EDLKN |
| 57 | LCAS | QLRLA | NSPLHFGNGTRLTVT (Jb 1.6) | EDLKN |
| 58 | LCASS | QLTLA | NSPLHFGNGTRLTVT (Jb 1.6) | EDLKN |
| 59 | LCASS | FLG | YNSPLHFGNGTRLTVT (Jb 1.6) | EDLKN |
| 60 | LCASS | QPTV | YNNEQFFGQRTRLLVL (Jb 2.1) | EDLKN |
| 61 | LCASS | SDGRM | STQYFGPGTRLLVL (Jb 2.3) | EDLKN |
| 62 | LCASS | LVAG | SIYEQYFGPGTRLTVT (Jb 2.7) | EDLKN |
| 63 | LCASS | SEREG | RAQYFGQGTRLTVL (Jb ?) | EDLKN |
| 64 | LCASS | GGEG | RAQYFGQGTRLTVL (Jb ?) | EDLKN |
| | KL-3 | | | |
| 65 | LCASS | LDGVP | YGYTFGSGTGLTVV (Jb 1.2) | EDLKN |
| 66 | LCASS | LDGVP | YGYTFGSGTRLTVV (Jb 1.2) | EDLKN |
| 67 | LCASS | LDGV | NYGYTFGSGTRLTVV (Jb 1.2) | EDLKN |
| 68 | LCASS | LVGRGP | YGYTFGSGTRLTVV (Jb 1.2) | EDLKN |
| 69 | LCASS | LGGVP | YGYTGSGTGLTVV (Jb 1.2) | EDLKN |
| 70 | LCASS | LRGTP | YGYTFGSGTRLTVV (Jb 1.2) | EDLKN |
| 71 | LCASS | QPAV | YNEQFFGPGTRLTVL (Jb 2.1) | EDLKN |
| 72 | LCASS | LELAG | YNEQFFGPGTRLTVL (Jb 2.1) | EDLKN |
| 73 | LCASS | LGGSEE | DTQYFGPGTRLTVL (Jb 2.3) | EDLKN |
| 74 | LCASS | LGGSE | ETQYFGPGTRLLVL (Jb 2.5) | EDLKN |
| 75 | LCASS | LGGSV | ETQYFGPGTRLLVL (Jb 2.5) | EDLKN |
| 76 | LCASS | LGSGTL | QETQYFGPGTRLLVL (Jb 2.5) | EDLKN |
| 77 | LCASS | LASGTL | QETQYFGPGTRLLVL (Jb 2.5) | EDLKN |
| 78 | LCASS | LASGTL | QETQYFGPGTRLLVL (Jb 2.5) | EDLKN |
| 79 | LCASS | PT | GANVLTFGAGSRLTVL (Jb 2.6) | EDLKN |
| 80 | LCASS | PT | GANVLTFGAGSRLTVL (Jb 2.6) | EDLKN |
| 81 | LCASS | QGS | TFGAGSRLTVL (Jb 2.6) | EDLKN |
| 82 | LCASS | | SGANVLTFGAGSRLTVL (Jb 2.6) | EDLKN |
| 83 | LCASS | L | GANVLTFGAGSRLTVL (Jb 2.6) | EDLKN |
| 84 | LCASS | LR | GANVLTFGAGSRLTVL (Jb 2.6) | EDLKN |
| 85 | LCASS | LVAG | SIYEQYFGPGTRLTVT (Jb 2.7) | EDLKN |
| 86 | LCASS | LVAG | SIYEQYFGPGTRLTVT (Jb 2.7) | EDLKN |
| 87 | LCASS | LVAG | SIYEQYFGPGTRLTVT (Jb 2.7) | EDLKN |
| | LJ1 | | | |
| 88 | LCAS | TLRL | GNSPLHFGNGTRLTVT (Jb 1.6) | EDLNK |
| 89 | LCASS | DSS | ETQYFGPGTRLLVL (Jb 2.5) | EDLKN |
| 90 | LCASS | LR | GANVLTFGAGSRLTVL (Jb 2.6) | EDLKN |
| 91 | LCASS | LR | GANVLTFGAGSRLTVL (Jb 2.6) | EDLKN |
| 92 | LCASS | PT | GANVLTFGAGSRLTVL (Jb 2.6) | EDLKN |
| 93 | LCASS | LVAGI | YEQYFGPGTRLTVT (Jb 2.7) | EDLKN |
| 94 | LCASS | LVAGSI | YEQYFGPSTRLTVT (Jb 2.7) | EDLKN |
| 95 | LCASS | LVAGSI | YEQYFGPSTRLTVT (Jb 2.7) | EDLKN |
| | Muscle infiltrating lymphocytes | | | |
| 96 | LCASS | LGSPGYR | TNEKLFFGSGTQLSVL (Jb 1.4) | EDLNK |
| 97 | LCASS | FTGAY | YNEQFFGPGTRLTVL (Jb 2.1) | EDLKN |
| 98 | LCASS | RRTSGFVH | DTQYFGPGTRLTVL (Jb 2.3) | EDLKN |
| 99 | LCAS | ARRTSGFV | TDTQYFGPGTRLTVL (Jb 2.3) | EDLKN |
| 100 | LCAS | TARRTSGFV | TDTQYFGPGTRLTVL (Jb 2.3) | EDLKN |
| 101 | LCA | TARRTSGFV | TDTQYFGPGTRLTVL (Jb 2.3) | EDLKN |
| 102 | LCA | TARRTSGFV | TDTQYFGPGTRLTVL (Jb 2.3) | EDLKN |
| 103 | LCA | TARRTSGFV | TDTQYFGPGTRLTVL (Jb 2.3) | EDLKN |
| 104 | LCA | TARRTSGFV | TDTQYFGPGTRLTVL (Jb 2.3) | EDLKN |
| 105 | LCAS | RQGART | GANVLTFGAGSRLTVL (Jb 2.6) | EDLKN |
| | JO (PBLs) | | | |
| 106 | LCASS | VALQDR | YGYTFGSGTGLTVV (Jb 1.2) | EDLNK |
| 107 | LCASS | TVRGS | QPQHFGDGTRLSIL (Jb 1.5) | EDLNK |
| 108 | LCASS | PGM | KNIQYFGAGTRLSVL (Jb 2.4) | EDLKN |
| 109 | LCASS | DSPSG | QETQYFGPGTRTVL (Jb 2.5) | EDLKN |
| 110 | LCASS | RPGNIR | ETQYFGPGTRLSVL (Jb 2.5) | EDLKN |
| 111 | LCASS | RSQGART | GANVLTFGAGSRLTVL (Jb 2.6) | EDLKN |
| | BM (PBLs) | | | |
| 112 | LCASS | DAG | YNSPLHFGNGTRLTVT (Jb 1.6) | EDLNK |
| 113 | LCASS | YTRQL | NSPLHFGNGTRLTVT (Jb 1.6) | EDLNK |

TABLE 7-continued

CDR3 Sequences of TCR Rearrangements
Amplified from NIS Brains and Controls

| Seq. ID | Vb5.2/3 | N-D-N | J | CB |
|---|---|---|---|---|
| 114 | LCASS | LEHRPT | AKNIQYFGAGTRLSVL (Jb 2.4) | EDLKN |
| 115 | LCASS | PER | GANVLTFGAGSRLTVL (Jb 2.6) | EDLKN |
| 116 | LCASS | QEA | SYEQYFGPGTRLTVT (JB 2.7) | EDLKN |
| 117 | LCAS | RLVRDLSH | EQYFGPSTRLTVT (Jb 2.7) | EDLKN |

Table 8 indicates the nucleotide sequence homology and the use of LRG or LGGE in the N-D-N-J region of the CDR3 loop. The table indicates from left to right: The sample, the sequence of the N-D-N-J region including the sequence encoding the afore indicated peptide sequences, the amino acid sequence, and the Vβ idiotype and the Jβ idiotype.

TABLE 8

Nucleotide Sequence Homology in the Use of LeuArgGly and LeuGlyGlyGlu

| Seq. ID | Sample | N—D—N—J | | | | | Seq. ID | | | | |
|---|---|---|---|---|---|---|---|---|---|---|---|
| 118 | KL3 | AGCAGC | | CTA CGC GGG GCC AAC | | | 138 | S S | | LRGAN | (Vb5.2/Jb2.6) |
| 119 | | AGCAGC | | TTA CGC GGG ACA CCC | | | 139 | S | | LRGTP | (Vb5.2/Jb1.2) |
| 120 | KL1 | AGCAGC | | TTG CGC TTG GCT AAT | | | 140 | SS | | LRLAN | (Vb5.2/Jb1.6) |
| 121 | | AGC | CAG | TTG CGC TTG GCT AAT | | | 141 | S | Q | LRLA | (Vb5.2/Jb1.6) |
| 122 | | AGCAGC | CAG | TTG CGC TTG GCT AAT | | | 142 | SS | Q | LRLA | (Vb5.2/Jb1.6) |
| 123 | | AGCAGC | | TTG GAT CGC TTG TAT AAT | | | 143 | SS | | LDRLA | (Vb5.2/Jb1.6) |
| 124 | LJ1 | AGC | ACG | TTG CGC TTG GGT | | | 144 | S | T | LRLG | (Vb5.2/Jb1.6) |
| 125 | | AGCAGC | | CTA CGG GGG GCC AAC | | | 145 | SS | | LRGAN | (Vb5.2/Jb2.6) |
| 126 | | AGCAGC | | CTA CGG GGG GCC AAC | | | 146 | SS | | LRGAN | (Vb5.2/Jb2.6) |
| 127 | MS18^ | ACGACG | | TTG AGG GGG GCG CTA | | | 147 | SS | | LRGAL | (Vb5.2/Jb2.4) |
| 128 | BF1* | AGCAGC | | CTC AGG GGG | | | 148 | SS | | LRG | (Vb6/Jb1.6) |
| 129 | E* | AGCAGC | | ATA AGG GGA AGC | | | 149 | SS | | IRGS | (Vb6/Jb2.7) |
| 130 | BD3* | AGCAGC | | ATC GTC AGG GGA TCG | | | 150 | SS | | IVRGS | (Vb6/Jb2.7) |
| 131 | ph11# | AGCAGT | | TTA AGG GCG GGA | | | 151 | SS | | LRAG | (Vb8/Jb1.1) |
| 132 | 12H6+ | AGCAGC | | CTC CGG GAC TTT | | | 152 | SS | | LRDF | (Vb13/Jb2.1) |
| 133 | KL3 | AGCAGC | | TTG GGA GGG GTA CCC TAT | | | 153 | SS | | LGGVPY | (Vb5.2/Jb1.2) |
| 134 | | AGCAGC | | TTG GGA GGG TCC GAA GAG | | | 154 | SS | | LGGSEE | (Vb5.2/Jb2.3) |
| 135 | | AGCAGC | | TTG GGA GGG TCC GAA GAG | | | 155 | SS | | LGGSEE | (Vb5.2/Jb2.5) |
| 136 | | AGCAGC | | TTG GGA GGG TCC GTT GAG | | | 156 | SS | | LGGSVE | (Vb5.2/Jb2.5) |
| 137 | 4@ | AGCAGC | | CTG GGG GGC GAA | | | 157 | SS | | LGGE | (Vb8.2/Jb2.5) |

^CDR3 usage in human MBP 88-99 specific T cell line (Martin et al., 1991 J.E.M. 173:19–24).
*CDR3 usage in rat spinal cord derived T cell clones specific for BP 85-99 (Gold et al., 1992 J.I. 148:1712–1717).
@CDR3 usage in rat lymph node derived T cell clone specific for BP 85-99 (Gold et al., 1992).
Cone derived from a human tonsil cDNA library (Tillinghast et al., 1986 Science 233:879–883).
+Noncytolytic mouse T cell clone specific for the influenza virus strain A/PR8/34 (Morahan et al., 1989).

TABLE 9

| | HLA CLASS II | | | | Cells/μl | |
|---|---|---|---|---|---|---|
| NM | DRB1 | DQA1 | DQB1 | DPB1 | CD4 | CD8 |
| PATIENTS | | | | | | |
| SLC | 0101/02,0401 | 0101,0301 | 0302,0501 | 0401,0401 | 760 | 530 |
| EWP | 0101/02,0401 | 0101,0301 | 0302,0501 | 0401,0401 | 850 | 640 |
| BLM | 0301,1301 | 0103,0501 | 0201,0603 | 0201,0402 | 1500 | 400 |
| NS | 0403,06,07 | 0201,0301 | 0302,0303 | 0401,0401 | 750 | 370 |
| SLB | 0101/02,1104 | 0101,0501 | 0301,0501 | 0301,0401 | 570 | 270 |
| SJP | 0101/02,1303 | 0101,0501 | 0301,0501 | 0301,0402 | 540 | 290 |
| LSH | 0103,1001 | 0101,0101 | 0501,0501 | 0401,0401 | 1200 | 300 |
| GAS | 0301,1303 | 0501,0501 | 0201,0301 | 0101,0101 | 620 | 270 |
| EV | 0404,0301 | 0301,0501 | 0201,0302 | 0101,0601 | 880 | 280 |
| JDM | 07,1503/04 | 0102,0201 | 0201,0602 | 0101,1001 | 680 | 470 |
| AM | 07,1501 | 0102,0101 | 0501,0501 | 0401,0401 | 560 | 360 |
| LC | 0301,1501 | 0102,0501 | 0201,0602 | 0301,0401 | 990 | 470 |

TABLE 9-continued

| CONTROLS | | | | | | | |
|---|---|---|---|---|---|---|---|
| SZ | 1104,1502 | | 0103,0103 | 0601,0603 | 0201,1401 | 610 | 540 |
| MB | 1501,- | | 0101,- | 0602,- | 0301,- | 1300 | 636 |
| IL | 07,1501 | | 0102,0201 | 0201,0602 | nd | nd | nd |
| RL | 0801,1501 | | 0102,0401 | 04,0501 | 0301/0301 | nd | nd |

| | % TCR+/CD8− | | | | | | | % TCR+/CD8+ | | | | | |
|---|---|---|---|---|---|---|---|---|---|---|---|---|---|
| NM | Vα2 | Vβ5a | Vβ5b | Vβ5c | Vβ6 | Vβ8 | Vβ12 | Vα2 | Vβ5a | Vβ5b | Vβ5c | Vβ6 | Vβ8 | Vβ12 |
| PATIENTS | | | | | | | | | | | | | | |
| SLC | 4.5 | 2.6 | 1.3 | 2.3 | 6.3 | 5.7 | 2.0 | 1.8 | 1.3 | 0.7 | 0.7 | 8.0 | 12.4 | 0.8 |
| EWP | 1.2 | 2.0 | 0.7 | 1.6 | 6.5 | 3.9 | 1.8 | 1.2 | 2.5 | 2.1 | 0.5 | 0.8 | 1.8 | 0.9 |
| BLM | 1.9 | 2.7 | 1.0 | 3.0 | 6.0 | 4.2 | 2.1 | 2.3 | 3.9 | 1.1 | 2.2 | 2.7 | 3.1 | 1.6 |
| NS | 3.3 | 2.0 | 0.8 | 2.7 | 1.8 | 3.2 | 1.9 | 3.3 | 1.4 | 0.7 | 1.3 | 0.5 | 4.2 | 0.8 |
| SLB | 2.7 | 3.2 | 2.4 | 1.6 | 6.1 | 4.7 | 2.1 | 2.7 | 3.1 | 0.9 | 1.0 | 2.3 | 3.3 | 1.2 |
| SJP | 4.5 | 3.5 | 2.4 | 4.0 | 4.9 | 5.0 | 2.8 | 3.1 | 2.0 | 0.9 | 1.1 | 1.1 | 8.1 | 1.8 |
| LSH | 5.1 | 1.6 | 0.9 | 4.8 | 2.8 | 4.5 | 2.3 | 2.3 | 1.7 | 0.5 | 1.2 | 0.8 | 3.4 | 1.5 |
| GAS | 2.9 | 3.3 | 1.5 | 4.1 | 4.3 | 5.4 | 2.5 | 2.0 | 2.4 | 1.0 | 1.5 | 1.6 | 5.6 | 1.5 |
| EV | 3.1 | 2.6 | nd | 2.9 | 5.8 | 5.2 | 2.2 | 0.9 | 1.9 | nd | 1.1 | 1.3 | 3.3 | 0.8 |
| JDM | 2.7 | 2.2 | 2.4 | 3.1 | 3.2 | 5.4 | 1.9 | 2.0 | 1.3 | 2.2 | 1.4 | 0.8 | 3.8 | 1.5 |
| AM | 1.6 | 2.8 | 1.2 | 1.6 | 5.6 | 3.6 | 1.2 | 1.1 | 2.0 | 0.8 | 0.6 | 1.7 | 2.8 | 0.6 |
| LC | 3.8 | 3.1 | 1.1 | 2.7 | 4.1 | 5.2 | 1.7 | 1.0 | 1.6 | 0.6 | 0.9 | 1.1 | 3.4 | 1.2 |
| CONTROLS | | | | | | | | | | | | | | |
| SZ | 3.1 | 2.8 | 1.0 | 3.6 | 6.1 | 3.3 | 2.2 | 5.9 | 3.9 | 0.6 | 2.2 | 3.7 | 2.5 | 1.6 |
| MB | 1.6 | 1.0 | 5.6 | 2.6 | 2.0 | 2.2 | 1.2 | 0.9 | 1.4 | 0.2 | 0.5 | 0.3 | 0.4 | 0.5 |
| IL | nd | 1.0 | 0.5 | nd | 2.3 | 4.9 | 2.1 | nd | 1.2 | 0.6 | nd | 1.3 | 3.3 | 1.5 |
| RL | nd | 1.6 | 0.7 | 2.9 | 2.0 | 4.8 | 3.3 | nd | 1.4 | 0.4 | 1.2 | 0.6 | 2.4 | 0.9 |

Flow Cytometry: Peripheral blood mononuclear cells (PBMC) were prepared by Ficoll-Hypaque density gradient centrifugation as described (Jackson and Warner, 1985). Briefly, 20 ml of blood at room temperature were diluted with an equal volume of saline, underlayered with Histopaque-1077-1 (Sigma, St. Louis, Mo.) and centrifuged 30 min. at 400 g. PBMC were washed twice by centrifugation at 250 g for 10 min with staining solution (saline containing 1% fetal calf serum). Three-color staining of 20 µl of $2\times10^7$ PBMC suspensions was performed in 96 well plates (Costar, Cambridge, Mass.) at 4° C. by incubating 20 µl of FITC-conjugated Diversi-T αβ TCR Screening Panel (T Cell Sciences, Cambridge, Mass.) monoclonal antibodies, 20 µl of phycoerythrin conjugated anti-Leu-3a (CD4) (Becton Dickinson, San Jose, Calif.) and 20 µl of PerCP anti-Leu-2a (CD8) (Becton Dickinson) for 30 min. The PBMC were washed three times in staining solution and fixed with 1% formaldehyde. Fluorescence analysis was carried out on a Becton Dickinson FACScan. The results of Table 9 were obtained as described above, from a number of patients and provide for the HLA idiotype, the ratio of CD4 T-cells and CD8 T-cells in the sample and the percent of cells having the particular subunit rearrangement in the group of cells staining for TCR+/CD8− and TCR+/CD8+. Comparing the patients with the controls, Vβ5a and Vβ5c for the CD8− cells would appear to be enhanced in the patients as compared to the controls. A similar pattern is seen in Vβ6. This pattern is absent in the CD8+ cells as compared to controls.

It is evident from the above results that the subject method can be used for identifying T-cell receptors associated with degenerative disorders. Thus, by a simple screening technique, one may identify those T-cell receptors which cause or combat disease and by various procedures inhibit or enhance their activity. The subject invention provides the capability to diagnose individuals susceptible to degenerative diseases associated with T-cell receptor variable regions. By screening degenerative tissue for T-cell receptors and identifying the specific T-cell receptors associated with that tissue and the HLA of the particular host, the relationship between the T-cell receptor, HLA and the disease may be established. Contrastingly, when the T-cells are associated with combatting a neoproliferative disorder, the particular T-cells may be employed for prophylaxis or therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the presence in a human host of T-cells associated with multiple sclerosis, said method comprising:

isolating T-cells from the brain or cerebrospinal fluid of a human host;

detecting in the T-cells of the brain or cerebrospinal fluid of said host the presence of a limited number of rearranged CDR3 regions of the T-cell receptor Valpha or Vbeta chain, wherein said rearrangement is associated with multiple sclerosis;

wherein the presence of T cells associated with said multiple sclerosis is determined.

2. A method according to claim 1, wherein said step of detecting comprises:

isolating nucleic acid from said T-cells;

combining said nucleic acid with a first primer specific for sequence 5' to a rearranged CDR3 and a second primer specific for sequence 3' to the rearranged CDR3 of T-cell receptor Valpha or Vbeta chains associated with multiple sclerosis;

amplifying nucleic acid that hybridizes with said primers by means of the polymerase chain reaction such that rearranged CDR3 regions are included within the amplified product; and determining the presence of a limited number of rearranged CDR3 regions.

3. A method according to claim 2, wherein one of said primers is for the Vβ 5.2 beta chain.

4. A method according to claim 1, wherein said Vbeta chain is Vβ 5.2.

5. A method for determining the presence in a human host of T-cells associated with multiple sclerosis, said method comprising:

isolating T-cells from the brain of a human host;

detecting in the T-cells of the brain of said host the presence of a limited number of rearranged CDR3 regions of the T-cell receptor Valpha or Vbeta chain, wherein said rearrangement is associated with multiple sclerosis;

wherein the presence of T cells associated with said multiple sclerosis is determined.

6. A method for determining the presence in a human host of T-cells associated with multiple sclerosis, said method comprising:

isolating nucleic acid from T-cells from the brain of said human host;

combining said nucleic acid with a first primer located 5' to a rearranged CDR3 and a second primer located 3' to the rearranged CDR3 of T-cell receptor Valpha or Vbeta chains, wherein said rearrangement is associated with multiple sclerosis;

amplifying nucleic acid that hybridizes with said primers by means of the polymerase chain reaction; and determining the presence of a limited number of rearranged CDR3 regions, thereby determining the presence in a human host of T-cells associated with multiple sclerosis.

* * * * *

UNITED STATES PATENT AND TRADEMARK OFFICE
CERTIFICATE OF CORRECTION

PATENT NO. : 5,667,967
DATED : September 16, 1997
INVENTOR(S) : Lawrence Steinman, et al.

It is certified that error appears in the above-identified patent and that said Letters Patent is hereby corrected as shown below:

On the cover page under item [54] after "RECEPTOR," please delete "VARIBLE" and substitute therefor --VARIABLE--.

Signed and Sealed this

Twenty-fourth Day of November, 1998

Attest:

BRUCE LEHMAN

Attesting Officer

Commissioner of Patents and Trademarks